United States Patent [19]
Nielsen et al.

[11] Patent Number: 5,977,296
[45] Date of Patent: Nov. 2, 1999

[54] CHIRAL PEPTIDE NUCLEIC ACID MONOMERS AND OLIGOMERS

[76] Inventors: Peter Nielsen, Hjortevanget 509, DK 2980 Kokkedal, Denmark; Ole Buchardt, deceased, late of DK 3500 Vaerlose, Denmark; by Mrs. D. Buchardt, Sondergardsvej 73, DK 3500 Vaerlose, Denmark; Pierre Lagriffoul, 7, Rue des Camelias, 81200 Mazamet, France

[21] Appl. No.: 08/366,231

[22] Filed: Dec. 28, 1994

Related U.S. Application Data

[63] Continuation-in-part of application No. 08/108,591, filed as application No. PCT/EP92/01219, May 22, 1992.

[30]    Foreign Application Priority Data

| May 24, 1991 | [DK] | Denmark | 986/91 |
| May 24, 1991 | [DK] | Denmark | 987/91 |
| Apr. 15, 1992 | [DK] | Denmark | 510/92 |
| May 22, 1992 | [WO] | WIPO | EP/01219 |

[51] Int. Cl.[6] ............... C07K 5/02; C07K 5/08; C07K 7/02; C12Q 1/68
[52] U.S. Cl. ............ 530/300; 435/6; 435/69.1; 436/501; 514/2; 514/44; 530/317; 530/350; 935/77; 935/78
[58] Field of Search ............ 435/6, 69.1, 810; 436/501; 514/44, 2; 530/300, 350, 317; 935/77, 78

[56]    References Cited

U.S. PATENT DOCUMENTS 5,340,716   8/1994   Ullman et al. ............ 435/6

FOREIGN PATENT DOCUMENTS

| WO 86/05518 | 9/1986 | WIPO . |
| WO 86/05519 | 9/1986 | WIPO . |
| WO 90/02749 | 3/1990 | WIPO . |
| WO 92/20702 | 11/1992 | WIPO . |
| WO 93/12129 | 6/1993 | WIPO . |
| WO 93/24507 | 12/1993 | WIPO . |

OTHER PUBLICATIONS

Akashi, M. and Takemoto, "New Aspects of Polymer Drugs", *Advances in Polymer Science* 1990, 97, 107–146.

Almarsson, O. et al., "Molecular Mechanics Calculations of the Structures of Polyamide Nucleic Acid DNA Duplexes and Triple Helical Hybrids", *PNAS USA* 1993, 90, 7518–7522.

Almarsson, O. et al., "Peptide Nucleic Acid (PNA) Conformation and Polymorphism in PNA–DNA and PNA–RNA Hybrids", *PNAS USA* 1993, 90, 9542–9546.

Brady, S.F. et al., "Large–scale synthesis of a cyclic hexapeptide analogue of somatostatin", *J. Org. Chem.* 1987, 52, 764–769.

Brown, S. et al., "NMR Solution Structure of a Peptide Nucleic Acid Complexed with RNA", *Science* 1994, 265, 777–780.

Buttrey, J. et al., "Synthetic analogues of polynucleotides–XII: the resolution of DL–β–(thymin–1–YL)alanine and polymerisation of the β–(thymin–1–YL) alanines", *Tetrahedron* 1975, 31, 73–75.

Chen, S. et al, "Molecular Dynamics and NMR Studies of Single–Stranded PNAs", *Tetrahedron Letters* 1994, 35(29), 5105–5108.

De Koning, H. and Pandit, "Unconventional Nucleotide Analogues. V. Derivatives of 6–(1–pyrimidinyl)–and 6–(9–purinyl)–2–aminocaproic Acid", *Recueil* 1971, 90, 874–884.

Demidov, Vadim et al., "Sequence Selective Double Strand DNA Cleavage by Peptide Nucleic Acid (PNA) Targeting Using Nuclease S1" *Nucl. Acids Res.* 1993 21(19), 2103–2107.

Doel et al., "An Approach to the Synthesis of Peptide Analogues of Oligonucleotides (Nucleopeptides)", *Tetrahedron Letters* 1969, 27, 2285–2288.

Doel et al., "The Synthesis of Peptides Containing Purine and Pyrimidine Derivatives of DL–Alanine", *Tetrahedron* 1974, 30, 2755–2759.

Dueholm, K. et al., "An Efficient Synthesis of BOC–Aminoacetaldehyde and its Application to the Synthesis of N–(2–BOC–Aminoethyl)glycine Esters", *Organic Prep. and Procedures Int.* 1993, 25(4), 457–461.

A. Boc$_2$O, Methyl Bromoacetate
B. Carboxymethyl Thymine, DCC/DhbtOH, Base Hydrolysis Dueholm, K. et al, "Peptide Nucleic Acid (PNA) with a Chiral Backbone Based on Alanine", *Bioorganic & Medicinal Chem. Letters* 1994, 4(8), 1077–1080.

Dueholm, K. et al, "Synthesis of Peptide Nucleic Acid Monomers Containing the Four Natural Nucleobases: Thymine, Cytosine, Adenine, and Guanine and Their Oligomerization", *J. of Org. Chem.* 1994, 59, 5767–5773.

Egholm, M. "Peptide nucleic acids (PNA). Oligonucleotide analogues with an achiral peptide backbone", *J. Am. Chem. Soc.* 1992, 114, 1895–1897.

Egholm et al., "PNA Hybridizes to Complementary Oligonucleotides Obeying the Watson–Crick Hydrogen–Bonding Rules", *Nature* 1993, 365, 566–568.

Flam, F., "Can DNA Mimics Improve on the Real Thing?", *Science* 1993, 262, 1647–1649.

Frank–Kamenetskii, "A Change of Backbone", *Nature* 1991, 354, 505.

Griffith, M. et al., "Single and Bis Peptide Nucleic Acids as Triplexing Agents: Binding and Stoichiometry", *J. Am. Chem. Soc.* 1995, 117, 831–832.

Hanvey, J.C. et al., "Antisense and Antigene Properties of Peptide Nucleic Acids", *Science* 1992, 258, 1481–1485.

Helene, C. and Toulme, "Specific Regulation of Gene Expression by Antisense, Sense and Antigene Nucleic Acids", *Biochimica et Biophysica Acta* 1990, 1049, 99–125.

Huang, S. et al., "Acyclic nucleic acid analogues: Synthesis and oligomerization of τ, 4–diamino–2–oxo–1 (2H) –pyrimidinepentanoic acid and, 4–diamino –2–oxo–1 (2H) –pyrimidinehexanoic acid", *J. Org. Chem.* 1991, 56, 6007–6018.

Hyrup, et al., "Modification of the Binding Affinity of Peptide Nucleic Acids (PNA). PNA with Extended Backbones Consisting of 2–Aminoethyl–β–alanine or 3–Aminopropylglycine Units", *J.Chem. Soc. Chem. Commun.* 1993, 518–519.

Hyrup, B. et al., "Structure–Activity Studies of the Binding of Modified Peptide Nucleic Acids (PNAs) to DNA", *J. Am. Chem. Soc.* 1994, 116, 7964–7970.

Kim, S. et al., "Right–Handed Triplex Formed between Peptide Nucleic Acid PNA–$T_8$ and Poly(dA) Shown by Linear and Circular Dichroism Spectroscopy", *J. Am. Chem. Soc.* 1993, 115(15), 6477–6481.

Kosynkina, L. et al., "A Convenient Synthesis of Chiral Peptide Nucleic Acid (PNA) Monomers", *Tetrahedron Letters* 1994, 35(29), 5173–5176.

Inaki, Y. and Takemoto, "Functionality and Applicability of Synthetic Acid Analysis," *Current Topics Polym. Sci* 1987, 1, 80–100.

Inaki, Y., "Synthetic Nucleic Acid Analogs", *Prog. Polym. Sci.* 1992, 17, 515–570.

Lagriffoul, P. et al., "The Synthesis, Co–oligomerization and Hybridization of a Thymine–Thymine Heterodimer Containing PNA", *Bioorganic & Medicinal Chemistry* 1994, 4(8), 1081–1082.

Leijon, M. et al., "Structural Characterization of PNA–DNA Duplexes by NMR. Evidence for DNA in a B–like Conformation", *Biochemistry* 1994, 33, 9820–9825.

Lu et al., "Synthesis of Polyesters Containing Nucleic Acid Base Derivatives as Pending Side Chains," *Journal of Polymer Science: Part A: Polymer Chemistry* 1986, 24, 525–536.

Mack, D. et al., "Design and Chemical Synthesis of a Sequence–Specific DNA–Cleaving Protein", *J. Am. Chem. Soc.* 1988, 110, 7572–7574.

Mollegaard, N. et al., "Peptide Nucleic Acid DNA Strand Displacement Loops as Artificial Transcription Promoters", *PNAS USA* 1994, 91, 3892–3895.

Nagae, S. et al., "Functional Monomers and Polymers. CLIV. Application of Nucleic Acid Base Containing Polymers to High Performance Liquid Chromatography", *Journal of Polymer Science: Part A: Polymer Chemistry* 1989, 27, 2593–2609.

Nielsen, P. et al., "Peptide nucleic Acids (PNAs): Potential Antisense and Anti–Gene Agents", *Anti–Cancer Drug Design* 1993, 8, 53–63.

Nielsen, P., "Peptide Nucleic Acids (PNA): Potential Antiviral Agents", *International Antiviral News* 1993, 1(3), 37–39.

Nielsen, P. et al., Peptide Nucleic Acids (PNA): Oligonucleotide Analogs With a Polyamide Backbone, in "Antisense Research and Applications", S.T. Crooke and B. Lebleu (eds) CRC Press, Boca Raton, FL 1993.

Nielsen, P., Peptide Nucleic Acid (PNA). A DNA Mimic with a Peptide Backbone, *Bioconjugate Chem.* 1994, 5, 3–7.

Nielsen, P., "Peptide Nucleic Acid (PNA): A Model Structure for the Primordial Genetic Material", *Origins of Life and Evolution of the Biosphere* 1993, 23, 323–327.

Nielsen, P. et al., "Sequence–Specific Transcription Arrest by Peptide Nucleic Acid Bound to the DNA Template Strand", *Gene* 1994, 149, 139–145.

Nielsen, P.E., et al., "Sequence–Selective Recognition of DNA by Strand Displacement with a Thymine–Substituted Polyamide", *Science* 1991, 254, 1497–1500.

Nielsen, Peter E. et al., "Photochemical Cleavage or DNA by Nitrobenzamides Linked to 9–Aminoacridine" *Biochem.* 1988 27, 6338–6343.

Nielsen, P. et al., "Sequence Specific Inhibition of DNA Restriction Enzyme Cleavage by PNA", *Nucleic Acids Research* 1993, 21(2), 197–200.

Matthews, J. and Kricka, "Analytical Strategies for the Use of DNA Probes", *Analytical Biochemistry* 1988, 169, 1–25.

Nollet, A.H.J. et al., "Unconventional Nucleotide Analogues—I $N^9$–Purinyl α–Amino Acids", *Tetrahedron* 1969, 25, 5971–5981.

Nollet, A.J.H. and Pandit, U.K., "Unconventional Nucleotide Analogues—II. Synthesis of the Adenyl Analogue of Willardiine", *Tetrahedron* 1969, 25, 5983–5987.

Nollet, A.J.H. and Pandit, "Unconventional Nucleotide Analogues—III. 4–($N^1$–pyrimidyl)–2–Aminobutyric Acids", *Tetrahedron* 1968, 25, 5989–5994.

Nollet, A.J.H. and Pandit, U.K., "Michael Addition of 4–O–Ethyluracil. A Method for specific $N_1$–Alkylation of Hydroxypyrimidines", *Tetrahedron Letters* 1969, 53, 4605–4606.

Orum, H. et al, "Single Base Pair Mutation Analysis by PNA Directed PCR Clamping", *Nucleic Acids Research* 1993, 21(23), 5332–5336.

Parkanyi, C. et al., "Synthesis of Polymethylene Chain-bridged 6–substituted 8–azapurines and Related Compounds", *Collect. Czech. Chem. Commun.* 1991, 56, 2382–2388.

Peffer, N. et al, "Strand–Invasion of Duplex DNA by Peptide Nucleic Acid Oligomers", *PNAS USA* 1993, 90, 10648–10652.

Pitha, P. et al., "Inhibition of murine leukemia virus replication by poly(vinyluracil) and poly(vinyladenine)", *PNAS USA* 1973, 70(4), 1204–1208.

Pitha, J., "Physiological activities of synthetic analogs of polynucleotides", *Advances in Polymer Science* 1983, 50, 1–16.

Pitha, J. et al., "Synthetic analogs of nucleic acids", *Biomedical Polymers* 1980, Eugene P. Goldberg and Nakajima (Editors), 271–297.

Rose, D.J., "Characterization of antisense binding properties of peptide nucleic acids by capillary gel electrophoresis", *Anal. Chem.* 65:3545–3548 (1993).

Simon, R. et al., "Peptoids: A modular approach to drug discovery", *PNAS USA* 1992, 89, 9367–9371.

Shvatschkin, Y.P. et al., "Ispechi i perspektivi chimij nikleominokislot y nikleopeptidov", *Ispechi Chimij* 1982, 2, 311–331.

Takemoto, K., "Recent problems concerning functional monomers and polymers containing nucleic acid bases", *Proceedings of the International Symposium on Polymeric Drugs* 1977, Mar. 20–25, 103–129.

Takemoto, K. and Inaki, Y "Synthetic Nucleic Acid Analogs. Preparation and Interactions", *Adv. Polym. Sci.* 41: 1–51 (Springer–Verlag, Berlin) (1981).

Uhlmann, E. and Peyman, A., "Antisense oligonucleotides: A new therapeutic principle", *Chemical Reviews* 1990, 90(4), 543–584.

Wakelin, Laurence P.G. et al., "Kinetic and Equilibrium Binding Studies of Amsacrine–4–Carboxamides: A Class of Asymmetrical DNA–Intercalating Agents which Bind by Threading Through the DNA Helix" *J. Med. Chem* 1990 33, 2039–2044.

Weller, D.D. and Daly, D.T., "Molecular modeling of acyclic polamide oligonucleotide analogues", *J. Org. Chem.* 1991, 56, 6000–6006.

Wittung, P. et al., "DNA–Like Double Helix Formed by Peptide Nucleic Acid", *Nature* 1994, 368, 561–563.

*Primary Examiner*—Ardin H. Marschel
*Attorney, Agent, or Firm*—Woodcock Washburn Kurtz Mackiewicz & Norris LLP

[57] ABSTRACT

A novel class of peptide nucleic acid monomers are synthesized having chirality in the backbone. Peptide nucleic acid oligomers are synthesized to incorporate these chiral monomers.

12 Claims, 2 Drawing Sheets

A. Boc₂O, Methyl Bromoacetate
B. Carboxymethyl Thymine, DCC/DhbtOH, Base Hydrolysis

CHIRAL PEPTIDE NUCLEIC ACID MONOMERS AND OLIGOMERS

CROSS REFERENCE TO RELATED APPLICATIONS

This application is a continuation-in-part of U.S. application Ser. No. 08/108,591, filed Nov. 22, 1993 that, in turn, is a national phase application of PCT application EP/01219, filed May 22, 1992, claiming priority to Danish Patent Applications: No. 986/91, filed May 24, 1991, No. 987/91, filed May 24, 1991, and No. 510/92, filed Apr. 15, 1992.

The contents of the foregoing patent applications are incorporated herein by reference.

FIELD OF THE INVENTION

This invention is directed to compounds that are not polynucleotides yet which bind to complementary DNA and RNA strands more strongly than the corresponding DNA. In particular, the invention concerns peptide nucleic acids (PNAs) which are synthesized to have a chiral backbone.

BACKGROUND OF THE INVENTION

Oligonucleotides and their analogs have been developed and used in molecular biology in certain procedures as probes, primers, linkers, adapters, and gene fragments. Modifications to oligonucleotides used in these procedures include labeling with non isotopic labels, e.g. fluorescein, biotin, digoxigenin, alkaline phosphatase, or other reporter molecules. Other modifications have been made to the ribose phosphate backbone to increase the nuclease stability of the resulting analog. These modifications include use of methyl phosphonates, phosphorothioates, phosphorodithioate linkages, and 2'-O-methyl ribose sugar units. Further modifications, include modifications made to modulate uptake and cellular distribution. Phosphorothioate oligonucleotides are presently being used as antisense agents in human clinical trials for various disease states including use as antiviral agents. With the success of these oligonucleotides for both diagnostic and therapeutic uses, there exists an ongoing demand for improved oligonucleotide analogs.

Oligonucleotides can interact with native DNA and RNA in several ways. One of these is duplex formation between an oligonucleotide and a single stranded nucleic acid. The other is triplex formation between an oligonucleotide and double stranded DNA to form a triplex structure.

Peptide nucleic acids are compounds that in certain respects are similar to oligonucleotide analogs however in other very important respects their structure is very different. In peptide nucleic acids, the deoxyribose backbone of oligonucleotides has been replaced with a backbone more akin to a peptide than a sugar. Each subunit, or monomer, has a naturally occurring or non naturally occurring base attached to this backbone. One such backbone is constructed of repeating units of N-(2-aminoethyl)glycine linked through amide bonds. Because of the radical deviation from the deoxyribose backbone, these compounds were named peptide nucleic acids (PNAs).

PNA binds both DNA and RNA to form PNA/DNA or PNA/RNA duplexes. The resulting PNA/DNA or PNA/RNA duplexes are bound with greater affinity than corresponding DNA/DNA or DNA/RNA duplexes as determined by Tm's. This high thermal stability might be attributed to the lack of charge repulsion due to the neutral backbone in PNA. The neutral backbone of the PNA also results in the Tm's of PNA/DNA(RNA) duplex being practically independent of the salt concentration. Thus the PNA/DNA duplex interaction offers a further advantage over DNA/DNA duplex interactions which are highly dependent on ionic strength. Homopyrimidine PNAs have been shown to bind complementary DNA or RNA forming (PNA) 2/DNA(RNA) triplexes of high thermal stability (see, e.g., Egholm, et al., Science, 1991, 254, 1497; Egholm, et al., J. Am. Chem. Soc., 1992, 114, 1895; Egholm, et al., J. Am. Chem. Soc., 1992, 114, 9677).

In addition to increased affinity, PNA has also been shown to bind to DNA with increased specificity. When a PNA/DNA duplex mismatch is melted relative to the DNA/DNA duplex there is seen an 8 to 20° C. drop in the Tm. This magnitude of a drop in Tm is not seen with the corresponding DNA/DNA duplex with a mismatch present.

The binding of a PNA strand to a DNA or RNA strand can occur in one of two orientations. The orientation is said to be anti-parallel when the DNA or RNA strand in a 5' to 3' orientation binds to the complementary PNA strand such that the carboxyl end of the PNA is directed towards the 5' end of the DNA or RNA and amino end of the PNA is directed towards the 3' end of the DNA or RNA. In the parallel orientation the carboxyl end and amino end of the PNA are just the reverse with respect to the 5'-3' direction of the DNA or RNA.

PNAs bind to both single stranded DNA and double stranded DNA. As noted above, in binding to double stranded DNA it has been observed that two strands of PNA can bind to the DNA. While PNA/DNA duplexes are stable in the antiparallel configuration, it was previously believed that the parallel orientation is preferred for $(PNA)_2$/DNA triplexes.

The binding of two single stranded pyrimidine PNAs to a double stranded DNA has been shown to take place via strand displacement, rather than conventional triple helix formation as observed with triplexing oligonucleotides. When PNAs strand invade double stranded DNA, one strand of the DNA is displaced and forms a loop on the side of the $PNA_2$/DNA complex area. The other strand of the DNA is locked up in the $(PNA)_2$/DNA triplex structure. The loop area (alternately referenced as a D loop) being single stranded, is susceptible to cleavage by enzymes that can cleave single stranded DNA.

A further advantage of PNA compared to oligonucleotides is that their polyamide backbone (having appropriate nucleobases or other side chain groups attached thereto) is not recognized by either nucleases or proteases and are not cleaved. As a result PNAs are resistant to degradation by enzymes unlike nucleic acids and peptides.

Because of their properties, PNAs are known to be useful in a number of different areas. Since PNAs having stronger binding and greater specificity than oligonucleotides, they are used as probes in cloning, blotting procedures, and in applications such as fluorescence in situ hybridization (FISH). Homopyrimidine PNAs are used for strand displacement in homopurine targets. The restriction sites that overlap with or are adjacent to the D-loop will not be cleaved by restriction enzymes. Also, the local triplex inhibits its gene transcription. Thus in binding of PNAs to specific restriction sites within a DNA fragment, cleavage at those sites can be inhibited. Advantage can be taken of this in cloning and subcloning procedures. Labeled PNAs are also used to directly map DNA molecules. In effecting this, PNA molecules having a fluorescent label are hybridized to complementary sequences in duplex DNA using strand invasion.

PNAs have further been used to detect point mutations in PCR-based assays (PCR clamping). PCR clamping uses PNA to detect point mutations in a PCR-based assay, e.g. the distinction between a common wild type allele and a mutant allele, in a segment of DNA under investigation. A PNA oligomer complementary to the wild type sequence is synthesized. The PCR reaction mixture contains this PNA and two DNA primers, one of which is complementary to the mutant sequence. The wild type PNA oligomer and the DNA primer compete for hybridization to the target. Hybridization of the DNA primer and subsequent amplification will only occur if the target is a mutant allele. With this method, one can determine the presence and exact identity of a mutant.

Considerable research is being directed to the application of oligonucleotides and oligonucleotide analogs that bind complementary DNA and RNA strands for use as diagnostics, research reagents and potential therapeutics. PCT/EP/01219 describes novel peptide nucleic acid (PNA) compounds which bind complementary DNA and RNA more tightly than the corresponding DNA. Because of these binding properties as well as their stability, such PNA compounds find many uses in diagnostics and reasearch reagents uses associated with both DNA and RNA. With complementary DNA and RNA they can form double-stranded, helical structures mimicking double-stranded DNA, and they are capable of being derivatized to bear pendant groups to further enhance or modulate their binding, cellular uptake, or other activity.

PNA compounds having cyclic backbones have been described by PCT/US93/05110. These compounds are believed to have increased conformational restriction which lends to increased binding affinity and specificity. However, these monomers, and oligomers comprising these monomers, are racemic mixtures which result in reduced binding specificity. Thus, compositions comprising single enantiomeric species and methods of making the same, are greatly desired.

OBJECTS OF THE INVENTION

It is an object of the invention to provide PNAs having a chiral backbone.

It is a further object of the present invention to provide PNA oligomers having at least one chiral PNA monomer.

It is yet a further object of the present invention to provide methods of producing these novel compounds.

These and other objects will become apparent from the following description and accompanying claims.

SUMMARY OF THE INVENTION

The present invention is directed to novel peptide nucleic acid monomers that contain an aliphatic cyclic structure in the backbone resulting in a chiral backbone. The present invention is also directed to peptide nucleic acid oligomers that incorporate these monomers.

Oligomers of the present invention are useful as research reagents and as diagostic tools. Compounds of the present invention can be used to detect point mutations in a sample of DNA of interest. Other applications include enabling PCR amplification of a mutant gene DNA while the wild type is suppressed by hybridization to a chiral PNA. Many applications of the present invention will become evident to those skilled in the art.

Compounds of the invention include peptide nucleic acid monomers of the formula:

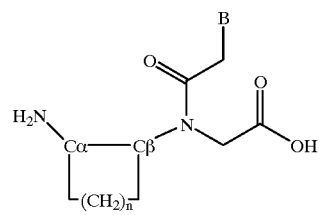

wherein:
B is a naturally or non-naturally ocurring nucleobase;
n is 0, 1, 2, or 3; and
at least one of Cα or Cβ is in the S configuration.

In a preferred embodiment of the invention both Cα and Cβ are in the S configuration.

In a further preferred embodiment of the invention B is adenine, cytosine, guanine, thymine, or uracil.

In still another preferred embodiment of the invention n is 2.

Further in accordance with this invention there are provided monomers of the formula:

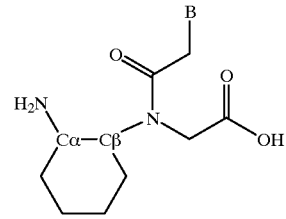

wherein:
B is a naturally or non-naturally ocurring nucleobase; and
at least one of Cα or Cβ is in the S configuration.

In a preferred embodiment of the invention Cα and Cβ are in the S configuration.

In a further preferred embodiment of the invention B is adenine, cytosine, guanine, thymine, or uracil.

Compounds of the invention further include peptide nucleic acid oligomers complementary to a target molecule. The oligomers comprise at least one peptide nucleic acid monomer having a (2-aminoethyl) glycine backbone with a chiral center in the ethyl portion of the backbone. The monomer is incorporated into peptide nucleic acid oligomers of the present invention at a position corresponding to a region of variability in the target molecule.

Further in accordance with the present invention there are provided oligomers comprising at least two peptide nucleic acid monomers, at least one of said peptide nucleic acid monomers having the structure:

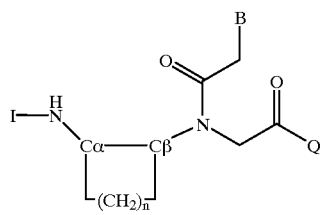

wherein:
B is a naturally or non-naturally ocurring nucleobase;
at least one of Cα or Cβ is in the S configuration;

Q is —OH, a carbonyl protecting group, or a covalent bond;

I is H, an amino protecting group, or a covalent bond; and n is 0, 1, 2, or 3.

In a preferred embodiment of the invention Cα and Cβ are in the S configuration.

In a further preferred embodiment of the invention B is adenine, cytosine, guanine, thymine, or uracil.

In yet a further preferred embodiment of the invention n is 2.

BRIEF DESCRIPTION OF THE FIGURES

FIG. I illustrates a synthetic scheme according to the invention and discussed in Examples 1–8.

FIG. II illustrates the circular dichroism spectra of chiral PNAs hybridized to their complementary DNAs.

DESCRIPTION OF PREFERRED EMBODIMENTS

Figure 1:
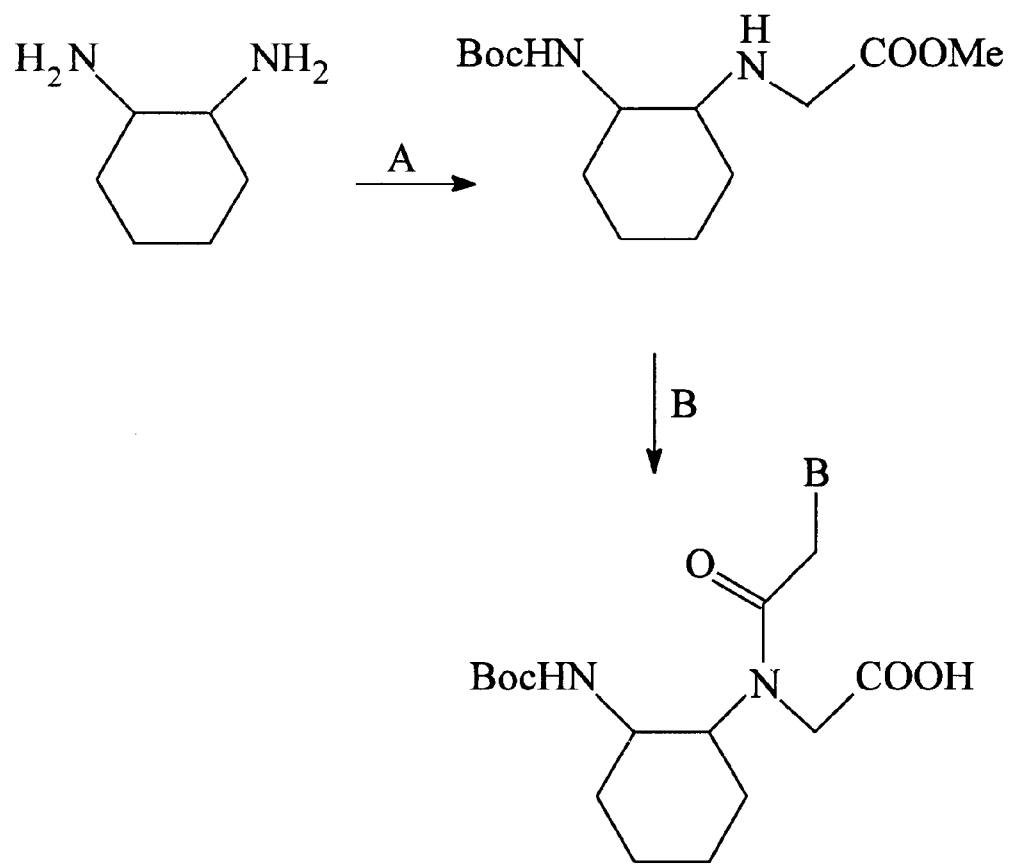

Specific sequence recognition of DNA or RNA is of increasing importance for the development of biological probes and new reagents for use in research (Uhlmann, E., Peyman, A., *Chem. Rev.*, 1990, 90, 544, and Helene, C., Toulme, J. J., *Biochim. Biophys. Acta.*, 1990, 1049, 99). Peptide nucleic acid (PNA), an achiral analog of DNA where the nucleobases or nucleobase analogs are attached to a (2-aminoethyl)-glycine backbone through a methylene carbonyl linker have properties making them well suited for use as biological probes and other applications. PNA have shown strong binding affinity and specificity to complementary DNA, sequence specific inhibition of DNA restriction enzyme cleavage and site specific in vitro inhibition of translation (Egholm, M., et. al., *Chem. Soc., Chem. Commun.*, 1993, 800; Egholm, M., et. al., *Nature*, 1993, 365, 566; Nielsen, M., et. al. *Nucl. Acids Res.*, 1993, 21, 197; and Hanvey, J. C., et. al., *Science*, 1992, 258, 1481). Modifications of PNA include extended backbones (Hyrup, B., et. al. *Chem. Soc., Chem. Commun.*, 1993, 518), extended linkers between the backbone and the nucleobase, reversal of the amido bond (Lagriffoul, P. H., et. al., *Biomed. Chem. Lett.*, 1994, 4, 1081), and the use of a chiral backbone based on alanine (Dueholm, K. L, et. al., *BioMed. Chem. Lett.*, 1994, 4, 1077).

This invention is directed to a modification of PNA that has increased specificity while maintaining comparable affinity. This is acheived by the introduction of chirality into the backbone through an aliphatic cyclic structure incorporated to include the Cα and Cβ of the 2-aminoethyl portion of the backbone. The resulting monomer has increased conformational restriction. The added aliphatic cyclic ring system is also expected to increase the lipophilicity of the monomer. Thus, this invention is directed to novel PNA molecules having a chiral backbone. Peptide nucleic acid monomers of the present invention have the formula:

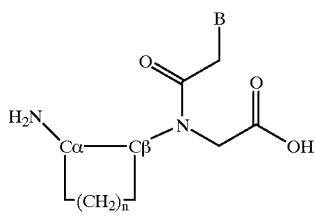

wherein:

B is a naturally or non-naturally ocurring nucleobase;

n is 0, 1, 2, or 3;

and at least one of Cα or Cβ is in the S configuration.

In some embodiments of the present invention B is a naturally occuring DNA nucleobase such as adenine, cytosine, guanine or thymine or other naturally occurring nucleobases (e.g., inosine, uracil, 5-methylcytosine or thiouracil). In still other embodiments of the present invention B is a non-naturally occuring nucleobase (e.g., bromothymine, azaadenines or azaguanines, etc.).

The Cα and Cβ of the 2-aminoethyl portion of the 2-aminoethylglycine backbone are synthesized to be part of an aliphatic cyclic structure. This aliphatic cyclic structure may be a 4, 5, 6 or 7 membered ring. In preferred embodiments the aliphatic cyclic structure is a 6 membered ring.

The use of optically active reagents permits the synthesis of pure SS, RR, SR, and RS isomers. The SS isomer is preferred in some embodiments of the present invention.

Monomers having a chiral backbone are prepared using (1,2)-diaminocyclohexane, which is available as the cis, or the trans isomer. The cis-(1,2)-diaminocyclohexane is a meso compound. Use of such meso compound requires purification of a racemic mixture. The trans-(1,2)-diaminocyclohexane is commercially available in enantiomerically pure form, making it well suited for monomers of predetermined chirality about both the Cα and the Cβ of the 2-aminoethyl portion of the backbone.

In FIG. I the diamine is protected at one of the amino groups with di-t-butylpyrocarbonate ($Boc_2O$), followed by N-alkylation with methyl bromoacetate to give the chiral backbone. Coupling of a carboxymethyl functionalized nucleobase (e.g. a 1-carboxymethyl pyrimidine, or a 9-carboxymethyl purine) or nucleobase analog with the chiral backbone using DCC/DhbtOH followed by basic hydrolysis will give the desired monomer containing a chiral backbone. In this manner the SS monomer, N-(2S-Boc-aminocyclohex-1S-yl)-N-(thymin-1-ylacetyl)-glycine and the RR monomer, N-(2R-Boc-aminocyclohex-1R-yl)-N-(thymin-1-ylacetyl)-glycine were synthesized. The RS and the SR isomers can be synthesized using the Cis-(1,2)-diaminocyclohexane and separating the racemic mixture that results. Separation can be achieved, for example, by liquid chromatography.

PNA oligomers comprising at least one chiral monomer are prepared in accordance with methods known to those skilled in the art. Established methods for the stepwise or fragmentwise solid-phase assembly of amino acids into peptides normally employ a beaded matrix of slightly cross-linked styrene-divinylbenzene copolymer, the cross-linked copolymer having been formed by the pearl polymerization of styrene monomer to which has been added a mixture of divinylbenzenes. A level of 1–2% cross-linking is usually employed. Such a matrix also can be used in solid-phase PNA synthesis in accordance with the present invention. Preferably, the PNA oligomer is prepared to be complementary to a target molecule, i.e. at least a portion of the PNA oligomer has the ability to hybridize due to Watson-Crick base pair attraction to the target molecule.

The thermal stability of homopyrimidine PNA/DNA and homopyrimidine PNA*/DNA wherein PNA* denotes a PNA oligomer containing one chiral (SS or RR) monomer was studied to determine the effects of the chiral monomer on the Tm. It has been previously shown that a homothymine PNA decamer forms a very stable 2:1 complex with its complementary DNA. Introduction of one mismatch in the DNA strand resulted in a significant destabilization of the PNA/DNA complex. When the SS isomer H-TTTTTTTTTT- Lys-NH$_2$ (SEQ ID NO:4) (where T denotes the SS monomer,N-(2S-Boc-aminocyclohex-1S-yl)-N-(thymin-1-ylacetyl)-glycine) was hybridized with the DNA 10 mer A$_{10}$, the Tm was comparable to that of the PNA(H-TTTTT**TTTTT-Lys-NH$_2$) (SEQ ID NO:4)/DNA complex. Introduction of a mismatch in the DNA 10 mer corresponding to the position of the chiral SS monomer in the chiral PNA 10 mer resulted in the same destabilization as the PNA without a chiral monomer present. The results of this study show that the 10 mer containing the SS isomer shows comparable binding affinity and equivalent specificity when compared to the 10 mer PNA without the SS isomer.

When the same thermal stability studies were performed on the RR isomer, N-(2R-Boc-aminocyclohex-1R-yl)-N-(thymin-1-ylacetyl) -glycine, there was seen poor binding affinity as well as poor specificity.

Circular dichroism and linear dichroism studies have shown that homopyrimidine PNA/DNA triplexes have a very similar structure to that of the conventional DNA/DNA triplex (Kim, S. K., et. al., *J. Am. Chem. Soc.,* 1993, 115, 6477). Figure II shows the CD spectra of the SS and the RR containing 10 mer PNAs hybridized to their complementary DNAs. The SS and RR containing 10 mers alone have a weak CD due to the presence of the chiral monomer and the L-Lys residue. Upon hybridization, a strong CD response, very much like that of the normal PNA/DNA complex, arose. In agreement with Tm studies, the SS containing 10 mer gave a stronger CD spectra that the RR containing 10 mer. Although the two chiral containing 10 mers are of different configuration, the complexes (SS 10 mer and RR 10 mer) gave rise to CD spectra that are not mirror-image. Thus, the incorporation of one chiral monomer did not disrupt the right-handed helical structure of the PNA/DNA complex.

The thermal stability of mixed PNA/DNA and mixed PNA*/DNA sequences wherein PNA* denotes a PNA oligomer containing one chiral (SS or RR) monomer was studied to determine the effects of the chiral monomer on the Tm. As illustrated in Example 28, when bound to an antiparallel DNA the oligomer containing the S,S-isomer showed comparable Tm to that of the unmodified PNA.

The thermal stability of a chiral PNA in a mixed sequence was determined. The PNAs H-GT*AGAT*CACT*-Lys-NH$_2$ SEQ ID NO:13, GTAGATCACT**-Lys-NH$_2$, SEQ ID NO:14, and GTAGATCACT-Lys-NH$_2$ SEQ ID NO:15 wherein denotes an SS monomer and a * denotes an RR monomer, were synthesized as per the general procedures of Example 25. Two DNA oligonucleotides were synthesized as per known-published procedures antiparallel to SEQ ID NO:15. These two DNA oligonucleotides differ in the base at position 6 such that one is complementary and the other is a single base mismatch. The mismatch ocurrs at a position that binds with a chiral position in the PNA oligomer. Each of the PNA oligomers e.g. the chiral PNA oligomers (R,R, and S,S) and the unmodified PNA oligomer were hybridized with each of the two DNA oligomers. The relative binding specificity was measured using the methods and apparatus of Example 28. The results show that the PNA 10 mer having an SS isomer shows greater specificity that the unmodified PNA 10 mer (23° C. versus 10° C.)

Oligomers of the present invention are useful as research reagents and as diagostic tools. PNAs have been used in studies to discriminate between fully complementary and single base mismatch targets (Orum, H., et. al., *Nucleic Acids Research,* 1993, 21, 5332–5336). The method utilizes the properties of PNA e.g. higher thermal stability, greater specificity when bound to complementary nucleic acid sequences than the corresponding deoxyribooligonucleotides and that PNAs are not recognized by DNA polymerase as primers. A PNA/DNA complex can effectively block the formation of a PCR product when the PNA is targeted against the PCR primer site. This method is effective in blocking target sequences when two target sequences in the same assay differ by only one base pair. Compounds of the present invention having greater specificity than normal PNA are well suited for use in diagnostic assays of this type. In preferred embodiments, it is preferred that at least one PNA monomer having a chiral center in the ethyl portion of the monomer is incorporated into the PNA oligomer at the site where a mismatch (i.e. variability of the target molecule) is expected or known to occur.

PNA oligomers having at least one chiral monomer are easily tagged with fluorescein or rhodamine using an aminohexanoic linking moiety. These tagged PNA oligomers are well suited for use as probes for a section of DNA of interest. Many other types of labeling reagents and linking moieties are amenable to the present invention. Many applications of the present invention will be evident to those skilled in the art.

The following examples are illustrative but are not meant to be limiting of the present invention.

EXAMPLE 1

(1S,2S)-1-(N-t-butyloxycarbonylamino)-2-aminocyclohexane (1)

To a cooled solution of (1S,2S)-diaminocyclohexane (5 ml; 41.6 mmol) in CH$_2$Cl$_2$ (25 ml) was added a solution of di-t-butyl dicarbonate (3.03 g; 13.9 mmol) in CH$_2$Cl$_2$ (25 ml) over a period of 30 mins. The reaction mixture was stirred overnight at room temperature. Water (20 ml) and CH$_2$Cl$_2$ (25 ml) were added in order to dissolve the precipitate. After separation of the two phases, the organic phase was concentrated under reduced pressure and the residue was dissolved in ether (25 ml) and water (25 ml). The mixture was acidified to pH 5 with HCl 4N and the bis-protected diamine was extracted with ether (3×25 ml). The aqueous phase was adjusted to 10.5 with NaOH 2N and extracted with ethylacetate (6×30 ml). The organic phase was dried over sodium sulfate, filtered and evaporated under reduced pressure to yield the title-compound (2.3 g, 73% based on Boc$_2$O).

mp: 109–111° C.; NMR$^1$H(dmso d6) ppm: 1.0–1.3 (m, 4H, 2CH$_2$ cycl); 1.45 (s, 9H, t-Boc); 1.6 (m, 2H, CH$_2$ cycl); 1.85 (m, 2H, CH$_2$ cycl); 2.4 (dt, 1H, CHN); 2.9 (m, 1H, CHN); 6.6 (m, 1H, NH carbamate); NMR $^{13}$C (dmso d6) ppm: 155.6 (carbamate); 77.4 (t-Boc); 57.0, 53.8, 34.4, 32.2, 25.8, 24.8 (C cycl); 28.4 (t-Boc).

EXAMPLE 2

N-(2S-Boc-aminocyclohex-1S-yl)-glycine, methyl ester (2)

To a cooled suspension of 1 (2 g, 9.35 mmol) and potassium carbonate (3.87 g, 28.05 mmol) in DMF (15 ml) was added a solution of methyl bromoacetate (0.9 ml, 9.35 mmol) in DMF (5 ml) over a period of 5 min. After one hour at 0° C. the salts were filtered and washed with DMF and CH$_2$Cl$_2$. The filtrate was evaporated under reduced pressure and the residue was purified by chromatography on silica gel (eluent ethylacetate). Yield: 1.9 g (70%).

mp: 68–70° C.; NMR$^1$H (dmso d6) ppm: 1.0–1.3 (m,4H, 2CH$_2$ cycl); 1.45 (s, 9H, t-Boc); 1.4–2.0 (m,5H,2CH$_2$ cycl+

NH); 2.3 (dt, 1H, CHN); 3.1 (m, 1H, CHN); 3.4 (dt, 2H, CH$_2$COO); 3.7 (s, 3H, COOCH$_3$); 6.7 (m, 1H, NH carbamate); NMR $^{13}$C (dmso d6) ppm: 172.9 (ester); 155.5 (carbamate); 77.5 (t-Boc); 59.7, 47.6 (CH$_2$COOCH$_3$); 53.7, 51.4, 32.1, 31.1, 24.6, 24.2 (C cyl); 28.3 (t-Boc); MSFAB+: 287.0 (M+1).

EXAMPLE 3

N-(2S-Boc-aminocyclohex-1S-yl)-N-(thymin-1-ylacetyl)-glycine, methyl ester (3)

To a solution of 2 (1.5 g, 5.24 mmol), thymine acetic acid (0.96 g; 5.22 mmol) and DhbtOH (0.85 g, 5.2 mmol) in DMF (15 ml) and CH$_2$Cl$_2$ (15 ml) was added DCC (1.08 g, 5.24 mmol). After 4 hrs at room temperature, DCU was filtered and washed with CH$_2$Cl$_2$ (100 ml). The filtrate was washed with NaHCO$_3$ 1M (3×40 ml), KHSO$_4$ 1M (2×40 ml), H$_2$O (40 ml). The organic phase was dried over sodium sulfate and filtered. Petroleum ether (100 ml) was added. After 48 h at 0° C., the title compound was collected by filtration. Yield: 1.7 g (72%).

mp: 205–207° C.; NMR $^1$H (dmso d6) ppm: 1.2–2.0 (m, CH$_2$ cycl); 1.45 (s, t-Boc); 1.9 (CH$_3$ thymine); 3.7 (s, COOCH$_3$); 3.7 (dd, CH$_2$COO); 4.8 (dd, CH$_2$-T); 6.95 (m, NH carbamate); 7.2 (s, H—C=C—Me); 11.35 (s, NH imide); NMR $^{13}$C (dmso d6) ppm: 169.7, 167.1, 164.3, 154.9, 150.9 (C=O); 141.5, 108.2 (C=C); 77.9 (t-Boc); 59.8 47.5 (CH$_2$COOCH$_3$); 53.7, 51.4, 32.1, 31.1, 24.6, 24.2 (C cycl); 28.2 (t-Boc); 11.9 (CH$_3$ thymine); MS FAB+: 453.3 (M+1); 353.3 (M+1 -t-Boc).

EXAMPLE 4

N-2-(2S-Boc-aminocyclohex-1S-yl)-N-(thymin-1-ylacetyl)-glycine (4)

The monomer ester 3 (1.5 g, 3.3 mmol) was suspended in THF (15 ml) and a solution of LiOH 0.5M (15 ml; 7.5 mmol) was added as well as water (5 ml). After 45 minutes at room temperature, water (10 ml) was added and the mixture washed with ethylacetate (2×10 ml). The aqueous phase was acidified to pH 3 and extracted with ethylacetate (4×120 ml). The organic phase was dried over sodium sulfate and evaporated under reduced pressure. Yield: 1.36 g (94%).

NMR $^1$H (dmso d6) ppm: 1.2–2.0 (m, CH$_2$ cycl); 1.45 (s, t-Boc); 1.9 (CH$_3$ thymine); 3.9 (dd, CH$_2$COO); 4.8 (dd, CH$_2$-T); 6.95 (m, NH carbamate); 7.2 (s, H—C=C—Me); 11.35 (s, NH imide); 12.4 (m, COOH); NMR $^{13}$C (dmso d6) ppm: 170.3, 166.8, 164.3, 155.0, 150.9 (C=O); 141.5, 108.1 (C=C); 77.9, 28.2 (t-Boc); 59.7, 49.9, 47.9, 44.2, 32.1, 29.7, 24.4, 24.3, (C cycl+2CH$_2$); 11.9 (CH$_3$ thymine); MS FAB+ 439.2 (M+1); 339.1 (M+1 - t-Boc).

EXAMPLE 5

N-4-Cbz cytosine (5)

Over a period of about 1 h, Cbz chloride (52 ml; 0.36 mol) was added dropwise to a suspension of cytosine (8, 20.0 g; 0.18 mol) in dry pyridine (1000 ml) at 0° C. under nitrogen in oven-dried equipment. The solution then was stirred overnight, after which the pyridine suspension was evaporated to dryness, in vacuo. Water (200 ml) and 4 N hydrochloric acid were added to reach pH ~1. The resulting white precipitate was filtered off, washed with water and partially dried by air suction. The still-wet precipitate was boiled with absolute ethanol (500 ml) for 10 min, cooled to 0° C., filtered, washed thoroughly with ether, and dried, in vacuo.

Yield 24.7 g (54%). M.p.>250° C. Anal. for C$_{12}$H$_{11}$N$_3$O$_3$. Found(calc.); C: 58.59 (58.77); H: 4.55 (4.52); N: 17.17 (17.13). No NMR spectra were recorded since it was not possible to get the product dissolved.

EXAMPLE 6

N-4-Cbz-N-1-carboxymethyl cytosine (6)

In a three necked round bottomed flask equipped with mechanical stirring and nitrogen coverage was placed methyl bromacetate (7.82 ml; 82.6 mmol) and a suspension of N-4-Cbz cytosine (5, 21.0 g; 82.6 mmol) and potassium carbonate (11.4 g; 82.6 mmol) in dry DMF (900 ml). The mixture was stirred vigorously overnight, filtered, and evaporated to dryness, in vacuo. Water (300 ml) and 4 N hydrochloric acid (10 ml) were added, the mixture was stirred for 15 minutes at 0° C., filtered, and washed with water (2×75 ml). The isolated precipitate was treated with water (120 ml), 2N sodium hydroxide (60 ml), stirred for 30 min, filtered, cooled to 0° C., and 4 N hydrochloric acid (35 ml) was added. The title compound was isolated by filtration, washed thoroughly with water, recrystallized from methanol (1000 ml) and washed thoroughly with ether. This afforded 7.70 g (31%) of pure compound. The mother liquor from the recrystallization was reduced to a volume of 200 ml and cooled to 0° C. This afforded an additional 2.30 g of a material that was pure by tlc but had a reddish color. M.p. 266–274° C. Anal. for C$_{14}$H$_{13}$N$_3$O$_5$. Found(calc.); C: 55.41 (55.45); H: 4.23 (4.32); N: 14.04 (13.86). $^1$H-NMR (90 MHz; DMSO-d$_6$): 8.02 ppm (d, J=7.32 Hz, 1H, H-6); 7.39 (s, 5H, Ph); 7.01 (d, J=7.32 Hz, 1H, H-5); 5.19 (s, 2H, PhCH$_2$—); 4.52 (s, 2H).

EXAMPLE 7

N-4-Cbz-N-1-carboxymethyl cytosine pentafluorophenyl ester (7)

N-4-Cbz-N-1-carboxymethyl-cytosine (6, 4.00 g; 13.2 mmol) and pentafluorophenol (2.67 g; 14.5 mmol) were mixed with DMF (70 ml), cooled to 0° C. with ice-water, and DCC (3.27 g; 15.8 mmol) was added. The ice bath was removed after 3 min and the mixture was stirred for 3 h at room temperature. The precipitated DCU was removed by filtration, washed with DMF, and the filtrate was evaporated to dryness, in vacuo (0.2 mmHg). The solid residue was treated with methylene chloride (250 ml), stirred vigorously for 15 min, filtered, washed twice with diluted sodium hydrogen carbonate and once with saturated sodium chloride, dried over magnesium sulfate, and evaporated to dryness, in vacuo. The solid residue was recrystallized from 2-propanol (150 ml) and the crystals were washed thoroughly with ether. Yield 3.40 g (55%). M.p. 241–245° C. Anal. for C$_{20}$H$_{12}$N$_3$F$_5$O$_5$. Found(calc.); C: 51.56 (51.18); H: 2.77 (2.58); N: 9.24 (8.95). $^1$H-NMR (90 MHz; CDCl$_3$): 7.66 ppm (d, J=7.63 Hz, 1H, H-6); 7.37 (s, 5H, Ph); 7.31 (d, J=7.63 Hz, 1H, H-5); 5.21 (s, 2H, PhCH$_2$—); 4.97 (s, 2H, NCH$_2$—). FAB-MS: 470 (M+1)

EXAMPLE 8

N-2-(2S-Boc-aminocyclohex-1S-yl)-N-(cytosin-1-ylacetyl)-glycine (8)

The title compound is synthesized as per the procedures of Examples 3 and 4 using the product from Example 7.

EXAMPLE 9

9-Carboxymethyl adenine ethyl ester (18)

Adenine (10.0 g, 74 mmol) and potassium carbonate (10.29 g, 74.0 mmol) were suspended in DMF and ethyl bromoacetate (8.24 ml, 74 mmol) was added. The suspension was stirred for 2.5 h under nitrogen at room temperature and then filtered. The solid residue was washed three times with DMF (10 ml). The combined filtrate was evaporated to dryness, in vacuo. The yellow-orange solid material was poured into water (200 ml) and 4 N HCl was added to pH≈6. After stirring at 0° C. for 10 min, the solid was filtered off, washed with water, and recrystallized from 96% ethanol (150 ml). The title compound was isolated by filtration and washed thoroughly with ether.

Yield 3.4 g (20%). M.p. 215.5–220° C. Anal. for $C_9H_{11}N_5O_2$ found (calc.): C: 48.86 (48.65); H: 5.01 (4.91); N: 31.66 (31.42). $^1$H-NMR (250 MHz; DMSO-$d_6$): (s, 2H, H-2 & H-8), 7.25 (b. s., 2H, $NH_2$), 5.06 (s, 2H, $NCH_2$), 4.17 (q, 2H, J=7.11 Hz, $OCH_2$) and 1.21 (t, 3H, J=7.13 Hz, $NCH_2$). $^{13}$C-NMR. 152.70, 141.30, 61.41, 43.97 and 14.07. FAB-MS. 222 (MH+). IR: Frequency in $cm^{-1}$ (intensity). 3855 (54.3), 3274 (10.4), 3246 (14.0), 3117 (5.3), 2989 (22.3), 2940 (33.9), 2876 (43.4), 2753 (49.0), 2346 (56.1), 2106 (57.1), 1899 (55.7), 1762 (14.2), 1742 (14.2), 1742 (1.0), 1671 (1.8), 1644 (10.9), 1606 (0.6), 1582 (7.1), 1522 (43.8), 1477 (7.2), 1445 (35.8) and 1422 (8.6). The position of alkylation was verified by X-ray crystallography on crystals, which were obtained by recrystallization from 96% ethanol.

Alternatively, 9-carboxymethyl adenine ethyl ester 9, can be prepared by the following procedure. To a suspension of adenine (50.0 g, 0.37 mol) in DMF (1100 ml) in 2 L three-necked flask equipped with a nitrogen inlet, a mechanical stirrer and a dropping funnel was added 16.4 g (0.407 mol) haxane washed sodium hydride- mineral oil dispersion. The mixture was stirred vigorously for 2 hours, then ethyl bromacetate (75 ml, 0.67 mol) was added dropwise over the course of 3 hours. The mixture was stirred for one additional hour, whereafter tlc indicated complete conversion of adenine. The mixture was evaporated to dryness at 1 mmHg and water (500 ml) was added to the oily residue which caused crystallization of the title compound. The solid was recrystallized from 60% ethanol (600 ml). Yield after drying 53.7 (65.6%). HPLC (215 nm) purity>99.5%.

EXAMPLE 10

N-6-Cbz-9-carboxymethyl adenine ethyl ester (10)

9-Carboxymethyladenine ethyl ester (9, 3.40 g, 15.4 mmol) was dissolved in dry DMF (50 ml) by gentle heating, cooled to 20° C., and added to a solution of N-ethyl-Cbzimidazole tetrafluoroborate (62 mmol) in methylene chloride (50 ml) over a period of 15 min with ice-cooling. Some precipitation was observed. The ice bath was removed and the solution was stirred overnight. The reaction mixture was treated with saturated sodium hydrogen carbonate (100 ml). After stirring for 10 min, the phases were separated and the organic phase was washed successively with one volume of water, dilute potassium hydrogen sulfate (twice), and with saturated sodium chloride. The solution was dried over magnesium sulfate and evaporated to dryness, in vacuo, which afforded 11 g of an oily material. The material was dissolved in methylene chloride (25 ml), cooled to 0° C., and precipitated with petroleum ether (50 ml). This procedure was repeated once to give 3.45 g (63%) of the title compound. M.p. 132–35° C. Analysis for $C_{17}H_{17}N_5O_4$ found (calc.): C: 56.95 (57.46); H: 4.71 (4.82); N: 19.35 (19.71). $^1$H-NMR (250 MHz; $CDCl_3$): 8.77 (s, 1H, H-2 or H-8); 7.99 (s, 1H, H-2 or H-8); 7.45–7.26 (m, 5H, Ph); 5.31 (s, 2H, N-C$\underline{H}_2$); 4.96 (s, 2H, Ph-C$\underline{H}_2$); 4.27 (q, 2H, J=7.15 Hz, C$\underline{H}_2$CH$_3$) and 1.30 (t, 3H, J=7.15 Hz, CH$_2$C$\underline{H}_3$). $^{13}$C-NMR: 153.09; 143.11; 128.66; 67.84; 62.51; 44.24 and 14.09. FAB-MS: 356 (MH+) and 312 (MH+–$CO_2$). IR: frequency in $cm^{-1}$ (intensity). 3423 (52.1); 3182 (52.8); 3115 (52.1); 3031 (47.9); 2981 (38.6); 1747 (1.1); 1617 (4.8); 15.87 (8.4); 1552 (25.2); 1511 (45.2); 1492 (37.9); 1465 (14.0) and 1413 (37.3).

EXAMPLE 11

N-6-Cbz-9-carboxymethyl adenine (11)

N-6-Cbz-9-carboxymethyladenine ethyl ester (10, 3.20 g; 9.01 mmol) was mixed with methanol (50 ml) cooled to 0° C. Sodium Hydroxide Solution (50 ml; 2N) was added, whereby the material quickly dissolved. After 30 min at 0° C., the alkaline solution was washed with methylene chloride (2×50 ml). The aqueous solution was brought to pH 1.0 with 4 N HCl at 0° C., whereby the title compound precipitated. The yield after filtration, washing with water, and drying was 3.08 g (104%). The product contained salt and elemental analysis reflected that. Anal. for $C_{15}H_{13}N_5O_4$ found (calc.): C: 46.32 (55.05); H: 4.24 (4.00); N: 18.10 (21.40) and C/N: 2.57 (2.56). $^1$H-NMR(250 MHz; DMSO-$d_6$): 8.70 (s, 2H, H-2 and H-8); 7.50–7.35 (m, 5H, Ph); 5.27 (s, 2H, N-C$\underline{H}_2$); and 5.15 (s, 2H, Ph-C$\underline{H}_2$). $^{13}$C-NMR. 168.77, 152.54, 151.36, 148.75, 145.13, 128.51, 128.17, 127.98, 66.76 and 44.67.IR (KBr) 3484 (18.3); 3109 (15.9); 3087 (15.0); 2966 (17.1); 2927 (19.9); 2383 (53.8); 1960 (62.7); 1739 (2.5); 1688 (5.2); 1655 (0.9); 1594 (11.7); 1560 (12.3); 1530 (26.3); 1499 (30.5); 1475 (10.4); 1455 (14.0); 1429 (24.5) and 1411 (23.6). FAB-MS: 328 (MH+) and 284 (MH+–$CO_2$). HPLC (215 nm, 260 nm) in system 1: 15.18 min, minor impurities all less than 2%.

EXAMPLE 12

N-2-(2S-Boc-aminocyclohex-1S-yl)-N-(adenin-1-ylacetyl)-glycine (8)

The title compound is synthesized as per the procedures of Example 3 and 4 using the product from Example 11.

EXAMPLE 13

2-Amino-6-chloro-9-carboxymethylpurine (13)

To a suspension of 2-amino-6-chloropurine (5.02 g; 29.6 mmol) and potassium carbonate (12.91 g; 93.5 mmol) in DMF (50 ml) was added bromoacetic acid (4.70 g; 22.8 mmol). The mixture was stirred vigorously for 20 h. under nitrogen. Water (150 ml) was added and the solution was filtered through Celite to give a clear yellow solution. The solution was acidified to a pH of 3 with 4 N hydrochloric acid. The precipitate was filtered and dried, in vacuo, over an appropriate drying agent. Yield (3.02 g; 44.8%). $^1$H-NMR (DMSO-d6): d=4.88 ppm (s,2H); 6.95 (s,2H); 8.10 (s,1H).

EXAMPLE 14

2-Amino-6-benzyloxy-9-carboxymethylpurine (14)

Sodium (2.0 g; 87.0 mmol) was dissolved in benzyl alcohol (20 ml) and heated to 130° C. for 2 h. After cooling to 0° C., a solution of 2-amino-6-chloro-9-carboxymethylpurine (13, 4.05 g; 18.0 mmol) in DMF (85 ml) was slowly added, and the resulting suspension stirred overnight at 20° C. Sodium hydroxide solution (1N, 100 ml) was added and the clear solution was washed with ethyl acetate (3×100 ml). The water phase then was acidified to a pH of 3 with 4 N hydrochloric acid. The precipitate was taken up in ethyl acetate (200 ml), and the water phase was extracted with ethyl acetate (2×100 ml). The combined organic phases were washed with saturated sodium chloride solution (2×75 ml), dried with anhydrous sodium sulfate, and taken to dryness by evaporation, in vacuo. The residue was recrystallized from ethanol (300 ml). Yield after drying, in vacuo, over an appropriate drying agent: 2.76 g (52%). M.p. 159–65° C. Anal. (calc., found) C (56.18; 55.97), H (4.38; 4.32), N (23.4; 23.10). $^1$H-NMR (DMSO-d$_6$): 4.82 ppm. (s,2H); 5.51 (s,2H); 6.45 (s,2H); 7.45 (m,5H); 7.82 (s,1H).

EXAMPLE 15

2-N- Cbz-6-benzyloxy-9-carboxymethylpurine (15)

2-Amino-6-benzyloxy-9-carboxymethylpurine is further protected with Rappaport's Reagent following standard procedures and purified by silica gel column chromatography.

EXAMPLE 16

N2-(2S-Boc-aminocyclohex-1S-yl)-N-(adenin-1-ylacetyl)-glycine (16)

The title compound is synthesized as per the procedures of Example 4 using the product from Example 15.

EXAMPLE 17

(1R,2R)-1-(N-t-butylcarbonylamino)-2-aminocyclohexane (17)

To a cooled solution of (1R,2R)-(−)-trans-1,2-diaminocyclohexane (5 ml; 41.6 mmol) in CH$_2$Cl$_2$ (25 ml) was added a solution of di-t-butyl dicarbonate (3.03 g, 13.9 mmol) in CH$_2$Cl$_2$ (25 ml) over a period of 30 mins. The reaction mixture was stirred overnight at room temperature. Water (20 ml) and CH$_2$Cl$_2$ (25 ml) were added in order to dissolve the precipitate. After separation, the organic phase was concentrated under reduced pressure and the residue dissolved in ether (25 ml) and water (25 ml). The mixture was acidified to pH 5 with HCl 4N and the bis-protected diamine was extracted with ether (3×25 ml). The aqueous phase was adjusted to pH 10.5 with NaOH 2N and extracted with ethylacetate (6×30 ml). The organic phase was dried over sodium sulfate, filtered and evaporated under reduced pressure to yield the title-compound (2.171 g, 69.5% based on Boc$_2$O)

mp: 109–111° C.; NMR $^1$H (dmso d6) ppm: 1.0–1.3 (m, 4H, 2CH$_2$ cycl); 1.45 (s, 9H, t-Boc); 1.6 (m, 2H, CH$_2$ cycl); 1.85 (m, 2H, CH$_2$ cycl); 2.4 (dt, 1H, CHN); 2.9 (m, 1H, CHN); 6.6 (m, 1H, NH carbamate); NMR $^{13}$C (dmso d6) ppm: 155.6 (carbamate); 77.4 (t-Boc); 57.0, 53.8, 34.4, 32.2, 25.8, 24.8 (C cycl); 28.4 (t-Boc).

EXAMPLE 18

N-(2R-Boc-aminocyclohex-1R-yl)-glycine, methyl ester (18)

To a cooled suspension of 17 (2 g, 9.35 mmol) and potassium carbonate (3.87 g, 28.05 mmol) in DMF (15 ml) was added a solution of methyl bromoacetate (0.9 ml, 9.35 ml) in DMF (5 ml) over a period of 5 min. After one hour at 0° C. the salts were filtered and washed with DMF (15 ml) and CH$_2$Cl$_2$ (15 ml). The filtrate was evaporated under reduced pressure and the residue was purified by chromatography on silica gel (eluent ethylacetate). Yield: 1.99 g (74%).

mp: 68–70° C.; NMR $^1$H (dmso d6) ppm: 1.0–1.3 (m, 4H, 2CH$_2$ cycl); 1.45 (s, 9H, t-Boc); 1.4–2.0 (m, 5H, 2CH$_2$ cycl+NH); 2.3 (dt, 1H, CHN); 3.1 (m, 1H, CHN); 3.4 (dt, 2H, CH$_2$COO); 3.7 (s, 3H, COOCH$_3$); 6.7 (m, 1H, NH carbamate); NMR $_{13}$C (dmso d6) ppm: 172.9 (ester); 155.5 (carbamate); 77.5 (t-Boc); 59.7, 47.6 (CH$_2$COOCH$_3$); 53.7, 51.4, 32.1, 31.1, 24.6, 24.2 (C cycl); 28.3 (t-Boc); MS FAB+: 287.0 (M+1).

EXAMPLE 19

N-(2R-Boc-aminocyclohex-1R-yl)-N-(thymin-1-ylacetyl)-glycine, methyl ester (19)

To a solution of 18 (1.5 g, 5.24 mmol), thymine acetic acid (0.96 g, 5.22 mmol) and DhbtOH (0.85 g, 5.2 mmol) in DMF (20 ml) and CH$_2$Cl$_2$ (15 ml) was added DCC (1.08 g, 5.24 mmol). After 4 hours at room temperature, DCU was filtered and washed with CH$_2$Cl$_2$ (100 ml). The filtrate was washed with NaHCO$_3$ 1M (3×40 ml), KHSO$_4$ 1 M (2×40 ml) H$_2$O (40 ml). The organic phase was dried over sodium sulfate and filtered. Petroleum ether (100 ml) was added. After 48 h at 0° C., the title compound was collected by filtration. Yield: 1.77 g (74%)

mp: 205–207° C.; NMR $^1$H (dmso d6) ppm: 1.2–2.0 (m, CH$_2$ cycl); 1.45 (s, t-Boc); 1.9 (CH$_3$ thymine); 3.7 (s, COOCH$_3$); 3.7 (dd, CH$_2$COO); 4.8 (dd, CH$_2$-T); 6.95 (m, NH carbamate); 7.2 (s, H—C=C—Me); 11.35 (s, NH imide); NMR $^{13}$C (dmso d6) ppm: 169.7, 167.1, 164.3, 154.9, 150.9 (C=O); 141.5, 108.2 (C=C); 77.9 (t-Boc); 59.8, 47.5 (CH$_2$COOCH$_3$); 53.7, 51.4, 32.1, 31.1, 24.6, 24.2 (C cycl); 28.2 (t-Boc); 11.9 (CH$_3$ thymine); MS FAB+: 453.3 (M+1); 353.3 (M+1 - t-Boc).

EXAMPLE 20

N-(2R-Boc-aminocyclohex-1R-yl)-N-(thymin-1-ylacetyl)-glycine (20)

The monomer ester 19 (1.5 g, 3.3 mmol) was suspended in THF (15 ml) and a solution of LiOH 0.5M (15 ml, 7.5 mmol) was added as well as water (5 ml). After 45 min at room temperature water (30 ml) was added and the mixture was washed with CH$_2$Cl$_2$ (3×30 ml). The aqueous phase was acidified to pH 2.5–3 and extracted with ethylacetate (6×120 ml). The organic phase was dried over sodium sulfate and evaporated under reduced pressure to give the title compound. Yield: 1.38 g (95%).

NMR $^1$H (dmso d6) ppm: 1.2–2.0 (m, CH$_2$ cycl) 1.45 (s, t-Boc); 1.9 (CH$_3$ thymine); 3.9 (dd, CH$_2$COO); 4.8 (dd, CH$_2$-T); 6.95 (m, NH carbamate); 7.2 (s, H—C=C—Me); 11.35 (s, NH imide); 12.4 (m, COOH); NMR $^{13}$C (dmso d6) ppm: 170.3, 166.8, 164.3, 155.0, 150.9 (C=O); 141.5, 108.1, (C=C); 77.9, 28.2 (t-Boc); 59.7, 49.9, 47.9, 44.2, 32.1, 29.7, 24.4, 24.3, (C cycl+2 CH$_2$); 11.9 (CH$_3$ thymine); MS FAB+: 439.2 (M+1); 339.1 (M+1 - t-Boc).

EXAMPLE 21

N-2-(2R-Boc-aminocyclohex-1R-yl)-N-(cytosin-1-ylacetyl)-glycine (21)

The title compound is synthesized as per the procedures of Examples 19 and 20 using the product from Example 7.

EXAMPLE 22

N-2-(2R-Boc-aminocyclohex-1R-yl)-N-(adenin-1-ylacetyl)-glycine (8)

The title compound is synthesized as per the procedures of Examples 19 and 20 using the product from Example 11.

EXAMPLE 23

N-2-(2R-Boc-aminocyclohex-1R-yl)-N-(adenin-1-ylacetyl)-glycine (16)

The title compound is synthesized as per the procedures of Examples 19 and 20 using the product from Example 15.

EXAMPLE 24

Synthesis of PNA Oligomers by Solid Phase, General Procedure

The functionalized resin is measured out to typically provide 0.1–1.0 millimoles of functionality, (functionalities attached to resins are commercially available through various sources e.g. Peptides International, Kentucky). This weight of resin is suspended in a 1:1 (v:v) dichloromethane:dimethylformamide solution (30 mL/1 g of resin) and allowed to swell for a period of time if desired. The solvent is then removed by filtration and the resin resuspended in trifluoroacetic acid (1 mL/1 gm of resin) and shaken for 3 minutes. The trifluoroacetic acid is removed by filtration and this step is repeated once. The resin is washed three times with a solution of 1:1 (v:v) dichloromethane:dimethylformamide. The resulting resin is resuspended in pyridine solution (5 mL/1 gm of resin) and vacuum filtered to remove the pyridine. This step is repeated once. This is followed by resuspension and filtration (designated "washing") using 1:1 (v:v) dichloromethane:dimethylformamide solution (5 mL/1 g of resin) this washing step is repeated twice. The resin is suspended in 1:1 (v:v) pyridine:dimethylformamide and to this suspension is added the desired PNA monomer (2–10 molar equivalents), TBTU (1.9–9.9 molar equivalents), and di-isopropylethylamine (5–20 molar equivalents) such that the final concentration of PNA monomer is 0.2M. The suspension is shaken for 15–60 minutes and the spent coupling solution is removed by filtration. The resin is washed with pyridine three times, and any unreacted amines are capped using Rapoport's Reagent, 5 equivalents in DMF for 5 minutes. The resin is then washed three times with pyridine followed by three washes with a solution of 1:1 (v:v) dichloromethane:dimethylformamide (5 mL/1 gm of resin). At this point, the resin is ready for the next coupling reaction and this procedure is repeated until the desired PNA is assembled on the resin.

Specific Examples of Amino Ethyl Glycine (aeg-) PNAs and aeg-PNA Derivatives Prepared by this General Method

| Resin Employed | aeg-PNA/aeg-PNA Derivative Prepared | |
| --- | --- | --- |
| Merrifield | $H_2N$-GCAT-COOH | (SEQ ID NO:1) |
| Lys Substituted Merrifield | $H_2N$-GCAT-Lys-COOH | (SEQ ID NO:2) |
| MBHA | $H_2N$-GCAT-CONH$_2$ | (SEQ ID NO:1) |
| Lys Substituted MBHA | $H_2N$-GCAT-Lys-CONH$_2$ | (SEQ ID NO:2) |

EXAMPLE 25

Oligomerization Using Chiral PNA Monomers

Solid phase synthesis of PNA oligomers having a chiral monomer was performed as per the procedures of Example 24. (4-methylbenzhydryl)amine (MBHA) resin was used with the initial loading at 0.1 meq/g using HBTU/DIEA in DMF/pyridine as a coupling reagent. The free PNAs were released from the resin with TFMSA, purified by HPLC and characterized by FAB-MS. [H-TTT TT$_{cycRR}$T TTT T-LysNH$_2$ (SEQ ID NO:3): M+1: calc. 2860.9; found 2862.0; H-TTT TT$_{cycSS}$T TTT T-LysNH$_2$ (SEQ ID NO:4): M+1: calc. 2860.9; found 2861.7].

Specific Examples of Amino Ethyl Glycine (aeg-) PNAs Having a Chiral Monomer Incorporated Therein, Prepared by this General Method;

H-TTTTT*TTTTT-Lys-NH$_2$SEQ ID NO:3

H-TTTTT**TTTTT-Lys-NH$_2$SEQ ID NO:4 wherein T** denotes the SS monomer, N-(2S-aminocyclohex-1S-yl)-N-(thymin-1-ylacetyl)-glycine residue and a T* denotes the RR monomer, N-(2R-aminocyclohex-1R-yl)-N-(thymin-1-ylacetyl)-glycine residue.

Specific Examples of Amino Ethyl Glycine (aeg-) PNAs Having a Chiral Monomer Incorporated Therein, That are Prepared by this General Method;

$H_2N$-GC** T-COOH

H2N-GTA G*T CAC T-COOHSEQ ID NO:5

$H_2N$-CCA**GGC UCA GAT-COOHSEQ ID NO:6

$H_2N$-CTG TCT CCA TCC TCT T**CA CT-COOHSEQ ID NO:7

$H_2N$-TGG GA*G CC*A TAG CGA GCC-COOHSEQ ID NO:8

$H_2N$-TCT GAG TAG CAG AGG AGC TAA G-COOHSEQ ID NO:9 wherein ** denotes an SS monomer and a * denotes an RR monomer as shown above except with mixed sequences.

EXAMPLE 26

Functionalization with Fluorescein

PNA oligomer SEQ ID NO:4 is synthesized as per the procedures of Example 25. The oligomer is further functionalized with an N-Boc-aminohexanoic acid using the general procedure of Example 24. The Boc group is removed with TFA as per the general procedures and the oligomer is further coupled with fluorescein-N-hydroxysuccinimide. The PNA oligomer is cleaved from the resin and purified by reverse phase HPLC to give;

F-AHA-TTTTT**TTTTT-Lys-NH$_2$SEQ ID NO:4 wherein F represents fluorescein, AHA represents an aminohexanoic acid linker and ** represents the SS monomer, N-(2S-aminocyclohex-1S-yl)-N-(thymin-1-ylacetyl)-glycine residue.

EXAMPLE 27

Functionalization with Rhodamine

As per the procedures of Example 26 rhodamine-N-hydroxysuccinimide is incorporated at the N terminus of PNA oligomer SEQ ID NO:4 to give;

R-AHA-TTTTT**TTTTT-Lys-NH$_2$SEQ ID NO:4 wherein R represents rhodamine, AHA represents an aminohexanoic acid linker and ** represents the SS monomer, N-(2S-aminocyclohex-1S-yl)-N-(thymin-1-ylacetyl)-glycine residue.

EXAMPLE 28

Thermal Stability Studies of Homopyrimidine PNA vs Homopyrimidine Chiral PNA Against DNA The thermal stability of PNA/DNA and PNA*/DNA wherein PNA* denotes a PNA oligomer containing one chiral (SS or RR) monomer was studied to determine the effects of the chiral monomer on the Tm. When the SS isomer H-TTTTTTTTTT-Lys-NH$_2$ (SEQ ID NO:4; T denoting the SS monomer, N-(2S-aminocyclohex-1S-yl)-N-(thymin-1-ylacetyl)-glycine residue) was hybridized with the DNA 10 mer A$_{10}$ (SEQ ID NO: 11), the Tm was comparable to that of the PNA(H-TTTTTTTTTT-Lys-NH$_2$; SEQ ID NO:10)/DNA complex. Results of hybridization of the DNA 10 mer with the PNA's were compared with hybridazation of the PNA's with the same 10 mer containing a mismatch corresponding to a position occupied by a chiral monomer in the chiral PNA strand.

The results of the study show that the 10 mer containing the SS isomer shows equivalent binding affinity and comparable specificity to PNA. When the same thermal stability studies were performed on the RR isomer H-TTTTT*TTTTT-Lys-NH$_2$, (SEQ ID NO:6; T* denoting the RR monomer, N-(2R-aminocyclohex-1R-yl)-N-(thymin-1-ylacetyl)-glycine residue), there was seen poor binding affinity as well as poor specificity. The results of these studies are shown in Table 1.

TABLE 1

| PNA | SEQ ID NO: | DNA | SEQ ID NO: Tm |
|---|---|---|---|
| H-TTTTT*TTTTT-LysNH$_2$ (R,R) | 6 | no DNA | — (7° C.) |
| H-TTTTT*TTTTT-LysNH$_2$ (R,R) | 6 | AAAAAAAAAA | 11 (43° C.) |
| H-TTTTT*TTTTT-LysNH$_2$ (R,R) | 6 | AAAACAAAAA | 12 (40° C.) |
| H-TTTTT**TTTTT-LysNH$_2$ (S,S) | 5 | no DNA | — — |
| H-TTTTT**TTTTT-LysNH$_2$ (S,S) | 5 | AAAAAAAAAA | 11 (73° C.) |
| H-TTTTT**TTTTT-LysNH$_2$ (S,S) | 5 | AAAACAAAAA | 12 (60° C.) |
| H-TTTTTTTTTT-LysNH$_2$ | 10 | AAAAAAAAAA | 11 (76° C.) |
| H-TTTTTTTTTT-LysNH$_2$ | 10 | AAAACAAAAA | 12 (63° C.) |

The melting temperatures (Tm) of PNA/DNA hybrids were determined on a Gilford Response apparatus. The conditions were 100 mM NaCl, 10 mM Na phosphate, 0.1 mM EDTA, pH=7. The following extinction cooeficients were used: A, 10.8; T, 8.8; C, 7.3;mL/mmol-cm for both DNA and PNA. The Tm values were determined from the maximum of the first derivative of the plot of A$_{260}$ versus temperature.

Figure 2:
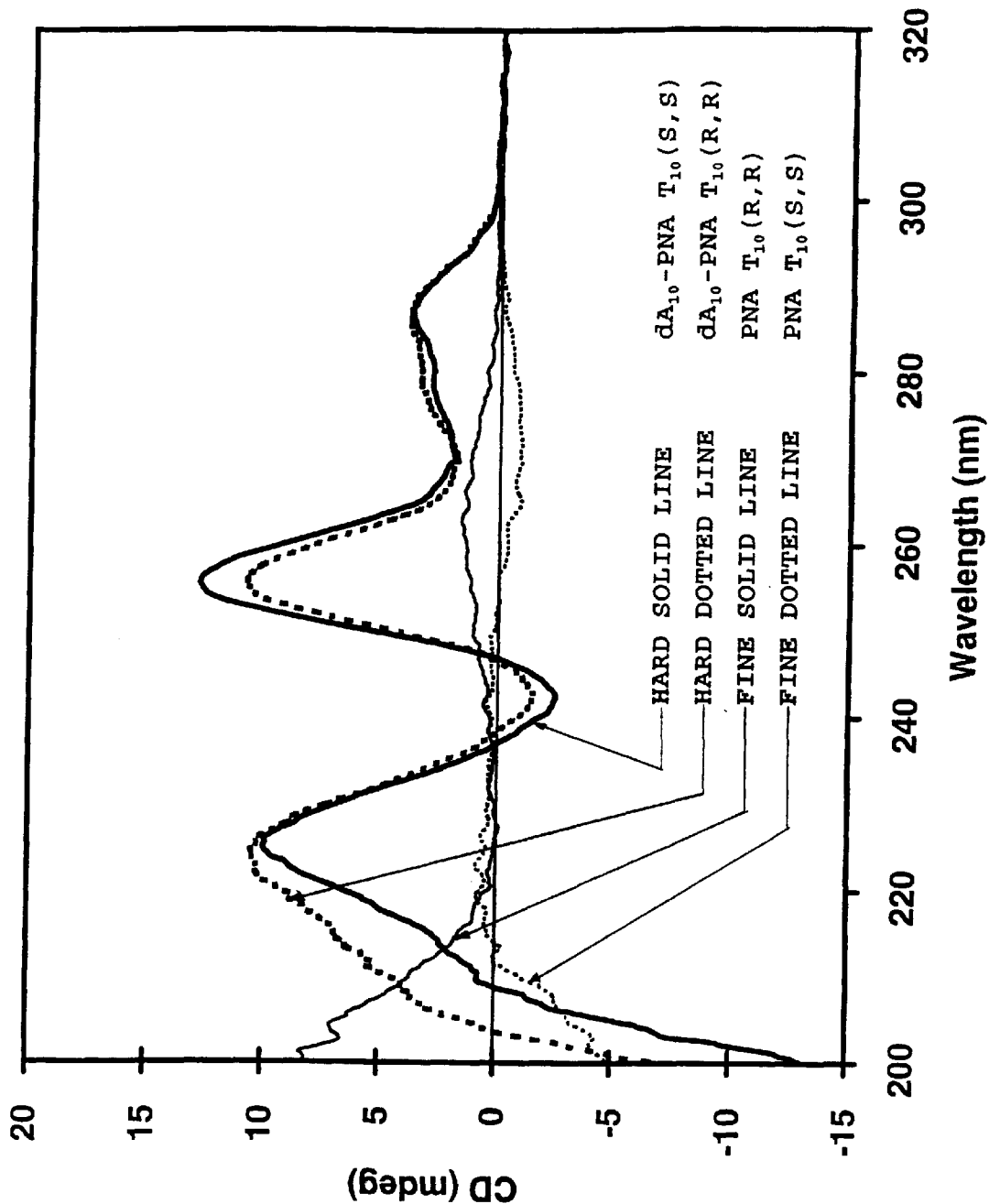

The circular dichroism spectra of PNA oligomer SEQ ID NO:4 and PNA oligomer SEQ ID NO:3 are shown in FIG. 2. The conditions for the spectra are 5 mM phosphate buffer pH 7.0, 25 μM basetriplets (2:1 PNA T$_{10}$ [SEQ ID NO:10] :dA$_{10}$ [SEQ ID NO: 11]). Incubation was for 1 hour prior to analysis. The spectra was run on a Jasco 720 instrument with a 2 nm bandpass, scan-rate 50 nm/min, 1 sec response time, with 6 averages of each spectrum. The temperature was maintained at 20° C. and the pathlength was 1 cm.

Homopyrimidine PNA$_2$/DNA triplexes are very similar in structure to that of the DNA/DNA triplexes (see, Kim, S. K., et. al., *J. Am. Chem. Soc.*, 1993, 115, 6477). As shown in the spectra PNA oligomer SEQ ID NO:4 and PNA oligomer SEQ ID NO:3 alone have a weak CD, due to chiral monomer and the L-lysine residue. Upon hybridization to the complementary DNA there is a strong CD response very similar to one that is obtained from a normal PNA/DNA complex. As expected from Tm experiments, the (S,S) isomer SEQ ID NO:4, gave a stronger CD spectra than the (R,R) isomer SEQ ID NO:3. The two CD spectra of the complexes formed from the (R,R) and (S,S) isomers are not mirror images. Thus, the incorporation of one chiral PNA monomer did not disrupt the right handed helical structure of the PNA/DNA complex.

EXAMPLE 29

Thermal Stability Studies Using a Mixed Sequence of PNA vs Chiral PNA

In a like manner to Example 28, the thermal stability of a chiral PNA in a mixed sequence was determined. The PNAs H-GT*AGAT*CACT*-Lys-NH$_2$ (SEQ ID NO:13), GTAGATCACT-Lys-NH$_2$ (SEQ ID NO:14), and GTAGATCACT-Lys-NH$_2$ (SEQ ID NO:15), wherein  denotes an SS monomer and * denotes an RR monomer, were synthesized in accordance with the general procedures of Example 25. DNA oligonucleotides CATCTAGTG (SEQ ID NO: 16) and CATCTGGTG (SEQ ID NO: 17) were synthesized in accordance with methods known in the art. Both SEQ ID NO: 16 and SEQ ID NO: 17 were antiparallel to SEQ ID NO:15 with the exception that SEQ ID NO: 17 included a single base mismatch at position 6, substituting a guanine for the complementary base pair adenine. The mismatch in SEQ ID NO: 17 ocurrs at a position that binds with a chiral position in the PNA oligomer, i.e. a chiral position was incorporated at position 6 in each of SEQ ID NO: 13 and SEQ ID NO: 14. The chiral PNA oligomers (R,R, and S,S) and the unmodified PNA oligomer were hybridized with each of the two DNA oligomers. Relative binding specificity was measured using the methods and apparatus of Example 28.

Results show that the PNA 10 mer containing the PNA isomer shows (S,S) exhibited greater specificity than the unmodified PNA 10 mer (23° C. T$_m$ versus 10° C. T$_m$, respectively). The PNA isomer (R,R) showed poor binding affinity as well as poor specificity. The results are outlined in Table 2.

TABLE 2

| OLIGOMER | 3'-CATCTAGTG-5' (SEQ ID NO:16) T$_m$ | 3'-CATCTGGTG-5' (SEQ ID NO:17) T$_m$ |
|---|---|---|
| H-GT*AGAT*CACT*-Lys-NH$_2$ (SEQ ID NO:13) (R,R) | 34° C. | no complex detected |
| GTAGATCACT**-Lys-NH$_2$ (SEQ ID NO:14) (S,S) | 50° C. | 27° C. |
| GTAGATCACT-Lys-NH$_2$ (SEQ ID NO:15) | 54° C. | 44° C. |

EXAMPLE 30

PCR Assay for the Detection of a Single Point Mutation

A multitude of human genetic diseases result from a single base mutation in a specific gene. PCR in vitro analysis of a tissue or cell sample using a PNA oligomer is performed as per the procedures contained in Orum, H., et. al., *Nucleic Acids Research,* 1993, 21, 5332–5336. Samples of interest are treated as per standard procedures to prepare genomic DNA for analysis. A PNA oligomer complementary to the wild type DNA in the region of interest is synthesized having a chiral PNA monomer at the position suspected of a point mutation. The sample is treated with an excess of this PNA oligomer and an excess of the appropriate primers bracketing the region of interest. The mutant gene is amplified and characterized utilizing the procedures refereced above and standard methods. If 100% of the target DNA is wild type no amplification will take place. If mutant DNA is present the mutant DNA will be amplified.

EXAMPLE 31

Detection of Mutant H-ras Gene Expression

Point mutations in the H-ras gene have been implicated in numerous aberrations of the Ras pathway. PNA oligomers are labeled after synthesis with fluorescein or other fluorescent tag. Labeled PNA oligomers are contacted with tissue or cell samples suspected of abnormal ras expression under conditions in which specific hybridization can occur, and the sample is washed to remove unbound PNA oligomer. Label remaining in the sample indicates bound PNA oligomer and is quantitated using a fluorimeter, fluorescence microscope or other routine means.

Tissue or cell samples suspected of expressing a point mutation in the H-ras gene are incubated with a fluorescein-labeled PNA oligomer which is targeted to the mutant codon 12, codon 13 or codon 61 of H-ras mRNA. An identical sample of cells or tissues is incubated with a second labeled PNA oligomer which is targeted to the same region of normal H-ras mRNA, under conditions in which specific hybridization can occur, and the sample is washed to remove unbound PNA oligomer. Label remaining in the sample indicates bound PNA oligomer and can be quantitated using a fluorimeter or other routine means. The presence of mutant H-ras is indicated if the first sample binds labeled PNA oligomer and the second sample does not bind fluorescent label.

Double labeling can also be used with PNA oligomers and methods of the invention to specifically detect expression of mutant ras. A single tissue sample is incubated with a rhodamine-labeled PNA oligomer which is targeted to codon 12, codon 13 or codon 61 of mutant H-ras mRNA and a fluorescein-labeled PNA oligomer which is targeted to the translation initiation site of ras mRNA, under conditions in which specific hybridization can occur. The sample is washed to remove unbound PNA oligomer and labels are detected by and fluorimetry with appropriate filters. The presence of mutant ras is indicated if the sample does not bind rhodamine-labeled PNA oligomer but does retain the fluorescein label.

EXAMPLE 32

Detection of Mutant β-Amyloid Precursor Protein Gene Expression (βAPP)

Point mutations in the gene encoding β-amyloid have been implicated in familial Alzheimer's disease (FAD). PNA oligomers are labeled after synthesis with fluorescein or other fluorescent tag. Labeled PNA oligomers are contacted with tissue or cell samples suspected of abnormal βAPP expression under conditions in which specific hybridization can occur, and the sample is washed to remove unbound PNA oligomers. Label remaining in the sample indicates bound oligonucleotide and is quantitated using a fluorimeter, fluorescence microscope or other routine means.

Tissue or cell samples suspected of expressing a point mutation in the βAPP gene are incubated with a fluorescein-labeled PNA oligomer which is targeted to the mutant codon 717, codon 670 or codon 671 of βAPP mRNA. An identical sample of cells or tissues is incubated with a second labeled PNA oligomer which is targeted to the same region of normal βAPP mRNA, under conditions in which specific hybridization can occur, and the sample is washed to remove unbound PNA oligomer. Label remaining in the sample indicates bound PNA oligomer and can be quantitated using a fluorimeter or other routine means. The presence of mutant βAPP is indicated if the first sample binds labeled PNA oligomer and the second sample does not bind fluorescent label.

Double labeling can also be used with PNA oligomers and methods of the invention to specifically detect expression of mutant βAPP. A single tissue sample is incubated with a rhodamine-labeled PNA oligomer which is targeted to codon 717, codon 670 or codon 671 of mutant βAPP mRNA and a fluorescein-labeled PNA oligomer which is targeted to the translation initiation site of mutant βAPP mRNA, under conditions in which specific hybridization can occur. The sample is washed to remove unbound PNA oligomer and labels are detected by and fluorimetry with appropriate filters. The presence of mutant βAPP is indicated if the sample does not bind rhodamine-labeled PNA oligomer but does retain the fluorescein label.

What is claimed is:

1. A peptide nucleic acid monomer having the formula:

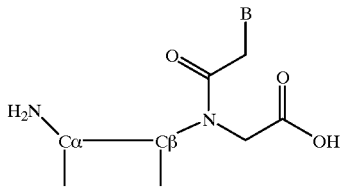

wherein:

B is a naturally or non-naturally ocurring nucleobase;

n is 0, 1, 2, or 3; and at least one of C$\alpha$ or C$\beta$ is in the S configuration.

2. The monomer of claim 1 wherein C$\alpha$ and C$\beta$ are in the S configuration.

3. The monomer of claim 1 wherein n is 2.

4. A peptide nucleic acid monomer having the formula:

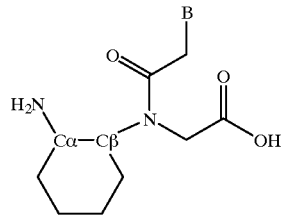

wherein:

B is a naturally or non-naturally ocurring nucleobase; and at least one of C$\alpha$ or C$\beta$ is in the S configuration.

5. The monomer of claim 4 wherein C$\alpha$ and C$\beta$ are in the S configuration.

6. A peptide nucleic acid oligomer complementary to a target molecule, said oligomer comprising at least one peptide nucleic acid monomer having a (2-aminoethyl) glycine backbone, wherein the C$\alpha$ and C$\beta$ carbons of said monomer form part of an alicyclic structure which renders said C$\alpha$ and C$\beta$ carbons chiral, said monomer being incorporated into the peptide nucleic acid oligomer at a position corresponding to a region of variability in the target molecule.

7. An oligomer comprising at least two peptide nucleic acid monomers, at least one of said peptide nucleic acid monomers having the structure:

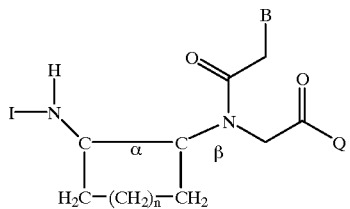

wherein:

B is a naturally or non-naturally ocurring nucleobase;

at least one of C$\alpha$ or C$\beta$ is in the S configuration;

Q is —OH, a carbonyl protecting group, or a covalent bond;

I is H, an amino protecting group, or a covalent bond; and n is 0, 1, 2, or 3.

8. The oligomer of claim 7 wherein C$\alpha$ and C$\beta$ are in the S configuration.

9. The oligomer of claim 7 wherein n is 2.

10. A peptide nucleic acid monomer having the formula:

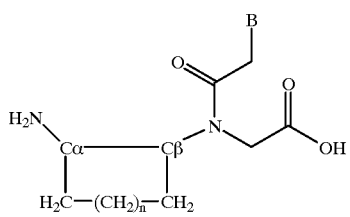

wherein:

B is adenine, cytosine, guanine, thymine, or uracil;

n is 0, 1, 2, or 3; and at least one of C$\alpha$ or C$\beta$ is in the S configuration.

11. A peptide nucleic acid monomer having the formula:

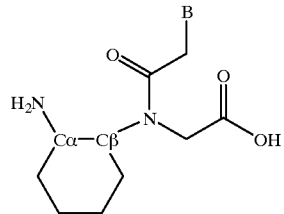

wherein:

B is adenine, cytosine, guanine, thymine, or uracil; and at least one of Cα or Cβ is in the S configuration.

12. An oligomer comprising at least two peptide nucleic acid monomers, at least one of said peptide nucleic acid monomers having the structure:

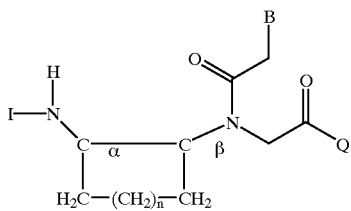

wherein:

B is adenine, cytosine, guanine, thymine, or uracil;

at least one of Cα or Cβ is in the S configuration;

Q is —OH, a carbonyl protecting group, or a covalent bond;

I is H, an amino protecting group, or a covalent bond; and n is 0, 1, 2, or 3.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 4
      (B) TYPE: amino acid
      (C) STRANDEDNESS: single (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= MODIFIED-SITE
                /note= N-(aminoethyl)-N-(guanin-1-ylacetyl)-
                glycine (ix) FEATURE:
            (A) NAME/KEY: Modified-site
            (B) LOCATION: 2
            (D) OTHER INFORMATION: /label= Modified-site
                /note= N-(aminoethyl)-N-(cytosin-1-ylacetyl)-
                glycine (ix) FEATURE:
            (A) NAME/KEY: Modified-site
            (B) LOCATION: 3
            (D) OTHER INFORMATION: /label= Modified-site
                /note= N-(aminoethyl)-N-(adenin-1-ylacetyl)-
                glycine (ix) FEATURE:
            (A) NAME/KEY: Modified-site
            (B) LOCATION: 4
            (D) OTHER INFORMATION: /label= Modified-site
                /note= N-(aminoethyl)-N-(thymin-1-ylacetyl)-
                glycine (xi) SEQUENCE DESCRIPTION: SEQ ID NO:1:

Xaa Xaa Xaa Xaa (2) INFORMATION FOR SEQ ID NO:2:

(i) SEQUENCE CHARACTERISTICS:
            (A) LENGTH: 5
            (B) TYPE: amino acid
            (C) STRANDEDNESS: single
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= MODIFIED-SITE
                /note= N-(aminoethyl)-N-(guanin-1-ylacetyl)-
                glycine (ix) FEATURE:
            (A) NAME/KEY: Modified-site
            (B) LOCATION: 2
            (D) OTHER INFORMATION: /label= Modified-site
                /note= N-(aminoethyl)-N-(cytosin-1-ylacetyl)-
                glycine (ix) FEATURE:
            (A) NAME/KEY: Modified-site
            (B) LOCATION: 3
            (D) OTHER INFORMATION: /label= Modified-site
                /note= N-(aminoethyl)-N-(adenin-1-ylacetyl)-
                glycine (ix) FEATURE:
            (A) NAME/KEY: Modified-site
            (B) LOCATION: 4
            (D) OTHER INFORMATION: /label= Modified-site
                /note= N-(aminoethyl)-N-(thymin-1-ylacetyl)-
                glycine (xi) SEQUENCE DESCRIPTION: SEQ ID NO:2:

Xaa Xaa Xaa Xaa Lys
 5

(2) INFORMATION FOR SEQ ID NO:3:

(i) SEQUENCE CHARACTERISTICS:
        (A) LENGTH: 11
        (B) TYPE: amino acid
        (C) STRANDEDNESS: single
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= MODIFIED-SITE
            /note= N-(aminoethyl)-N-(thymin-1-ylacetyl)-
            glycine (ix) FEATURE:
        (A) NAME/KEY: Modified-site
        (B) LOCATION: 2
        (D) OTHER INFORMATION: /label= MODIFIED-SITE
            /note= N-(aminoethyl)-N-(thymin-1-ylacetyl)-
            glycine (ix) FEATURE:
        (A) NAME/KEY: Modified-site
        (B) LOCATION: 3
        (D) OTHER INFORMATION: /label= MODIFIED-SITE
            /note= N-(aminoethyl)-N-(thymin-1-ylacetyl)-
            glycine (ix) FEATURE:
        (A) NAME/KEY: Modified-site
        (B) LOCATION: 4
        (D) OTHER INFORMATION: /label= MODIFIED-SITE
            /note= N-(aminoethyl)-N-(thymin-1-ylacetyl)-
            glycine (ix) FEATURE:
        (A) NAME/KEY: Modified-site
        (B) LOCATION: 5
        (D) OTHER INFORMATION: /label= MODIFIED-SITE
            /note= N-(2R-aminocyclohex-1R-yl)-N-(thymin-
            1-ylacetyl)-glycine (ix) FEATURE:
        (A) NAME/KEY: Modified-site
        (B) LOCATION: 6
        (D) OTHER INFORMATION: /label= MODIFIED-SITE
            /note= N-(aminoethyl)-N-(thymin-1-ylacetyl)-
            glycine (ix) FEATURE:
        (A) NAME/KEY: Modified-site
        (B) LOCATION: 7
        (D) OTHER INFORMATION: /label= MODIFIED-SITE
            /note= N-(aminoethyl)-N-(thymin-1-ylacetyl)-
            glycine (ix) FEATURE:
        (A) NAME/KEY: Modified-site
        (B) LOCATION: 8
        (D) OTHER INFORMATION: /label= MODIFIED-SITE
            /note= N-(aminoethyl)-N-(thymin-1-ylacetyl)-
            glycine (ix) FEATURE:
        (A) NAME/KEY: Modified-site
        (B) LOCATION: 9
        (D) OTHER INFORMATION: /label= MODIFIED-SITE
            /note= N-(aminoethyl)-N-(thymin-1-ylacetyl)-
            glycine (ix) FEATURE:
        (A) NAME/KEY: Modified-site
        (B) LOCATION: 10
        (D) OTHER INFORMATION: /label= MODIFIED-SITE
            /note= N-(aminoethyl)-N-(thymin-1-ylacetyl)-
            glycine (xi) SEQUENCE DESCRIPTION: SEQ ID NO:3:

Xaa Xaa Xaa Xaa Xaa Xaa Xaa Xaa Xaa Xaa Lys
1               5                   10

(2) INFORMATION FOR SEQ ID NO:4:

(i) SEQUENCE CHARACTERISTICS:
        (A) LENGTH: 11
        (B) TYPE: amino acid
        (C) STRANDEDNESS: single
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= MODIFIED-SITE
            /note= N-(aminoethyl)-N-(thymin-1-ylacetyl)-
            glycine (ix) FEATURE:
        (A) NAME/KEY: Modified-site
        (B) LOCATION: 2
        (D) OTHER INFORMATION: /label= MODIFIED-SITE
            /note= N-(aminoethyl)-N-(thymin-1-ylacetyl)-
            glycine (ix) FEATURE:
        (A) NAME/KEY: Modified-site
        (B) LOCATION: 3
        (D) OTHER INFORMATION: /label= MODIFIED-SITE
            /note= N-(aminoethyl)-N-(thymin-1-ylacetyl)-
            glycine (ix) FEATURE:
        (A) NAME/KEY: Modified-site
        (B) LOCATION: 4
        (D) OTHER INFORMATION: /label= MODIFIED-SITE
            /note= N-(aminoethyl)-N-(thymin-1-ylacetyl)-
            glycine (ix) FEATURE:
        (A) NAME/KEY: Modified-site
        (B) LOCATION: 5
        (D) OTHER INFORMATION: /label= MODIFIED-SITE
            /note= N-(2S-aminocyclohex-1S-yl)-N-(thymin-
            1-ylacetyl)-glycine (ix) FEATURE:
        (A) NAME/KEY: Modified-site
        (B) LOCATION: 6
        (D) OTHER INFORMATION: /label= MODIFIED-SITE
            /note= N-(aminoethyl)-N-(thymin-1-ylacetyl)-
            glycine (ix) FEATURE:
        (A) NAME/KEY: Modified-site
        (B) LOCATION: 7
        (D) OTHER INFORMATION: /label= MODIFIED-SITE
            /note= N-(aminoethyl)-N-(thymin-1-ylacetyl)-
            glycine (ix) FEATURE:
        (A) NAME/KEY: Modified-site
        (B) LOCATION: 8
        (D) OTHER INFORMATION: /label= MODIFIED-SITE
            /note= N-(aminoethyl)-N-(thymin-1-ylacetyl)-
            glycine (ix) FEATURE:
        (A) NAME/KEY: Modified-site
        (B) LOCATION: 9
        (D) OTHER INFORMATION: /label= MODIFIED-SITE
            /note= N-(aminoethyl)-N-(thymin-1-ylacetyl)-
            glycine

```
        (ix) FEATURE:
              (A) NAME/KEY: Modified-site
              (B) LOCATION: 10
              (D) OTHER INFORMATION: /label= MODIFIED-SITE
                    /note= N-(aminoethyl)-N-(thymin-1-ylacetyl)-
                    glycine (xi) SEQUENCE DESCRIPTION: SEQ ID NO:4:

Xaa Xaa Xaa Xaa Xaa Xaa Xaa Xaa Xaa Xaa Lys
1               5                   10

(2) INFORMATION FOR SEQ ID NO:5:

(i) SEQUENCE CHARACTERISTICS:
              (A) LENGTH: 9
              (B) TYPE: amino acid
              (C) STRANDEDNESS: single
              (D) TOPOLOGY: unknown (ii) MOLECULE TYPE: peptide (ix) FEATURE:
              (A) NAME/KEY: Modified-site
              (B) LOCATION: 1
              (D) OTHER INFORMATION: /label= MODIFIED-SITE
                    /note= N-(aminoethyl)-N-(guanin-1-ylacetyl)-
                    glycine (ix) FEATURE:
              (A) NAME/KEY: Modified-site
              (B) LOCATION: 2
              (D) OTHER INFORMATION: /label= MODIFIED-SITE
                    /note= N-(aminoethyl)-N-(thymin-1-ylacetyl)-
                    glycine (ix) FEATURE:
              (A) NAME/KEY: Modified-site
              (B) LOCATION: 3
              (D) OTHER INFORMATION: /label= MODIFIED-SITE
                    /note= N-(aminoethyl)-N-(adenin-1-ylacetyl)-
                    glycine (ix) FEATURE:
              (A) NAME/KEY: Modified-site
              (B) LOCATION: 4
              (D) OTHER INFORMATION: /label= MODIFIED-SITE
                    /note= N-(2R-aminocyclohex-1R-yl)-N-(guanin-
                    1-ylacetyl)-glycine (ix) FEATURE:
              (A) NAME/KEY: Modified-site
              (B) LOCATION: 5
              (D) OTHER INFORMATION: /label= MODIFIED-SITE
                    /note= N-(aminoethyl)-N-(thymin-1-ylacetyl)-
                    glycine (ix) FEATURE:
              (A) NAME/KEY: Modified-site
              (B) LOCATION: 6
              (D) OTHER INFORMATION: /label= MODIFIED-SITE
                    /note= N-(aminoethyl)-N-(cytosin-1-ylacetyl)-
                    glycine (ix) FEATURE:
              (A) NAME/KEY: Modified-site
              (B) LOCATION: 7
              (D) OTHER INFORMATION: /label= MODIFIED-SITE
                    /note= N-(aminoethyl)-N-(adenin-1-ylacetyl)-
                    glycine (ix) FEATURE:
              (A) NAME/KEY: Modified-site
              (B) LOCATION: 8
              (D) OTHER INFORMATION: /label= MODIFIED-SITE
                    /note= N-(aminoethyl)-N-(cytosin-1-ylacetyl)-
                    glycine (ix) FEATURE:
```

-continued (A) NAME/KEY: Modified-site
        (B) LOCATION: 9
        (D) OTHER INFORMATION: /label= MODIFIED-SITE
            /note= N-(aminoethyl)-N-(thymin-1-ylacetyl)-
            glycine (xi) SEQUENCE DESCRIPTION: SEQ ID NO:5:

Xaa Xaa Xaa Xaa Xaa Xaa Xaa Xaa Xaa
1               5

(2) INFORMATION FOR SEQ ID NO:6:

(i) SEQUENCE CHARACTERISTICS:
        (A) LENGTH: 12
        (B) TYPE: amino acid
        (C) STRANDEDNESS: single
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= MODIFIED-SITE
            /note= N-(aminoethyl)-N-(cytosin-1-ylacetyl)-
            glycine (ix) FEATURE:
        (A) NAME/KEY: Modified-site
        (B) LOCATION: 2
        (D) OTHER INFORMATION: /label= MODIFIED-SITE
            /note= N-(aminoethyl)-N-(cytosin-1-ylacetyl)-
            glycine (ix) FEATURE:
        (A) NAME/KEY: Modified-site
        (B) LOCATION: 3
        (D) OTHER INFORMATION: /label= MODIFIED-SITE
            /note= N-(2S-aminocyclohex-1S-yl)-N-(adenin-
            1-ylacetyl)-glycine (ix) FEATURE:
        (A) NAME/KEY: Modified-site
        (B) LOCATION: 4
        (D) OTHER INFORMATION: /label= MODIFIED-SITE
            /note= N-(aminoethyl)-N-(guanin-1-ylacetyl)-
            glycine (ix) FEATURE:
        (A) NAME/KEY: Modified-site
        (B) LOCATION: 5
        (D) OTHER INFORMATION: /label= MODIFIED-SITE
            /note= N-(aminoethyl)-N-(guanin-1-ylacetyl)-
            glycine (ix) FEATURE:
        (A) NAME/KEY: Modified-site
        (B) LOCATION: 6
        (D) OTHER INFORMATION: /label= MODIFIED-SITE
            /note= N-(aminoethyl)-N-(cytosin-1-ylacetyl)-
            glycine (ix) FEATURE:
        (A) NAME/KEY: Modified-site
        (B) LOCATION: 7
        (D) OTHER INFORMATION: /label= MODIFIED-SITE
            /note= N-(aminoethyl)-N-(uracil-1-ylacetyl)-
            glycine (ix) FEATURE:
        (A) NAME/KEY: Modified-site
        (B) LOCATION: 8
        (D) OTHER INFORMATION: /label= MODIFIED-SITE
            /note= N-(aminoethyl)-N-(cytosin-1-ylacetyl)-
            glycine (ix) FEATURE:
        (A) NAME/KEY: Modified-site 5,977,296

31

-continued

```
              (B) LOCATION: 9
              (D) OTHER INFORMATION: /label= MODIFIED-SITE
                  /note= N-(aminoethyl)-N-(adenin-1-ylacetyl)-
                  glycine (ix) FEATURE:
              (A) NAME/KEY: Modified-site
              (B) LOCATION: 10
              (D) OTHER INFORMATION: /label= MODIFIED-SITE
                  /note= N-(aminoethyl)-N-(guanin-1-ylacetyl)-
                  glycine (ix) FEATURE:
              (A) NAME/KEY: Modified-site
              (B) LOCATION: 11
              (D) OTHER INFORMATION: /label= MODIFIED-SITE
                  /note= N-(aminoethyl)-N-(adenin-1-ylacetyl)-
                  glycine (ix) FEATURE:
              (A) NAME/KEY: Modified-site
              (B) LOCATION: 12
              (D) OTHER INFORMATION: /label= MODIFIED-SITE
                  /note= N-(aminoethyl)-N-(thymin-1-ylacetyl)-
                  glycine (xi) SEQUENCE DESCRIPTION: SEQ ID NO:6:

Xaa Xaa Xaa Xaa Xaa Xaa Xaa Xaa Xaa Xaa Xaa Xaa
1               5                   10

(2) INFORMATION FOR SEQ ID NO:7:

(i) SEQUENCE CHARACTERISTICS:
              (A) LENGTH: 20
              (B) TYPE: amino acid
              (C) STRANDEDNESS: single
              (D) TOPOLOGY: unknown (ii) MOLECULE TYPE: peptide (ix) FEATURE:
              (A) NAME/KEY: Modified-site
              (B) LOCATION: 1
              (D) OTHER INFORMATION: /label= MODIFIED-SITE
                  /note= N-(aminoethyl)-N-(cytosin-1-ylacetyl)-
                  glycine (ix) FEATURE:
              (A) NAME/KEY: Modified-site
              (B) LOCATION: 2
              (D) OTHER INFORMATION: /label= MODIFIED-SITE
                  /note= N-(2S-aminocyclohex-1S-yl)-N-(thymin-
                  1-ylacetyl)-glycine (ix) FEATURE:
              (A) NAME/KEY: Modified-site
              (B) LOCATION: 3
              (D) OTHER INFORMATION: /label= MODIFIED-SITE
                  /note= N-(aminoethyl)-N-(guanin-1-ylacetyl)-
                  glycine (ix) FEATURE:
              (A) NAME/KEY: Modified-site
              (B) LOCATION: 4
              (D) OTHER INFORMATION: /label= MODIFIED-SITE
                  /note= N-(aminoethyl)-N-(thymin-1-ylacetyl)-
                  glycine (ix) FEATURE:
              (A) NAME/KEY: Modified-site
              (B) LOCATION: 5
              (D) OTHER INFORMATION: /label= MODIFIED-SITE
                  /note= N-(aminoethyl)-N-(cytosin-1-ylacetyl)-
                  glycine (ix) FEATURE:
              (A) NAME/KEY: Modified-site
              (B) LOCATION: 6
```

(D) OTHER INFORMATION: /label= MODIFIED-SITE
                /note= N-(aminoethyl)-N-(thymin-1-ylacetyl)-
                glycine (ix) FEATURE:
         (A) NAME/KEY: Modified-site
         (B) LOCATION: 7
         (D) OTHER INFORMATION: /label= MODIFIED-SITE
             /note= N-(aminoethyl)-N-(cytosin-1-ylacetyl)-
             glycine (ix) FEATURE:
         (A) NAME/KEY: Modified-site
         (B) LOCATION: 8
         (D) OTHER INFORMATION: /label= MODIFIED-SITE
             /note= N-(aminoethyl)-N-(cytosin-1-ylacetyl)-
             glycine (ix) FEATURE:
         (A) NAME/KEY: Modified-site
         (B) LOCATION: 9
         (D) OTHER INFORMATION: /label= MODIFIED-SITE
             /note= N-(aminoethyl)-N-(adenin-1-ylacetyl)-
             glycine (ix) FEATURE:
         (A) NAME/KEY: Modified-site
         (B) LOCATION: 10
         (D) OTHER INFORMATION: /label= MODIFIED-SITE
             /note= N-(2S-aminocyclohex-1S-yl)-N-(thymin-
             1-ylacetyl)-glycine (ix) FEATURE:
         (A) NAME/KEY: Modified-site
         (B) LOCATION: 11
         (D) OTHER INFORMATION: /label= MODIFIED-SITE
             /note= N-(aminoethyl)-N-(cytosin-1-ylacetyl)-
             glycine (ix) FEATURE:
         (A) NAME/KEY: Modified-site
         (B) LOCATION: 12
         (D) OTHER INFORMATION: /label= MODIFIED-SITE
             /note= N-(aminoethyl)-N-(cytosin-1-ylacetyl)-
             glycine (ix) FEATURE:
         (A) NAME/KEY: Modified-site
         (B) LOCATION: 13
         (D) OTHER INFORMATION: /label= MODIFIED-SITE
             /note= N-(aminoethyl)-N-(thymin-1-ylacetyl)-
             glycine (ix) FEATURE:
         (A) NAME/KEY: Modified-site
         (B) LOCATION: 14
         (D) OTHER INFORMATION: /label= MODIFIED-SITE
             /note= N-(aminoethyl)-N-(cytosin-1-ylacetyl)-
             glycine (ix) FEATURE:
         (A) NAME/KEY: Modified-site
         (B) LOCATION: 15
         (D) OTHER INFORMATION: /label= MODIFIED-SITE
             /note= N-(aminoethyl)-N-(thymin-1-ylacetyl)-
             glycine (ix) FEATURE:
         (A) NAME/KEY: Modified-site
         (B) LOCATION: 16
         (D) OTHER INFORMATION: /label= MODIFIED-SITE
             /note= N-(2S-aminocyclohex-1S-yl)-N-(thymin-
             1-ylacetyl)-glycine (ix) FEATURE:
         (A) NAME/KEY: Modified-site
         (B) LOCATION: 17
         (D) OTHER INFORMATION: /label= MODIFIED-SITE
             /note= N-(aminoethyl)-N-(cytosin-1-ylacetyl)-
             glycine

```
        (ix) FEATURE:
              (A) NAME/KEY: Modified-site
              (B) LOCATION: 18
              (D) OTHER INFORMATION: /label= MODIFIED-SITE
                  /note= N-(aminoethyl)-N-(adenin-1-ylacetyl)-
                  glycine (ix) FEATURE:
              (A) NAME/KEY: Modified-site
              (B) LOCATION: 19
              (D) OTHER INFORMATION: /label= MODIFIED-SITE
                  /note= N-(aminoethyl)-N-(cytosin-1-ylacetyl)-
                  glycine (ix) FEATURE:
              (A) NAME/KEY: Modified-site
              (B) LOCATION: 20
              (D) OTHER INFORMATION: /label= MODIFIED-SITE
                  /note= N-(aminoethyl)-N-(thymin-1-ylacetyl)-
                  glycine (xi) SEQUENCE DESCRIPTION: SEQ ID NO:7:

Xaa Xaa Xaa Xaa Xaa Xaa Xaa Xaa Xaa Xaa Xaa Xaa Xaa Xaa
1               5                   10

Xaa Xaa Xaa Xaa Xaa Xaa
15              20

(2) INFORMATION FOR SEQ ID NO:8:

(i) SEQUENCE CHARACTERISTICS:
              (A) LENGTH: 18
              (B) TYPE: amino acid
              (C) STRANDEDNESS: single
              (D) TOPOLOGY: unknown (ii) MOLECULE TYPE: peptide (ix) FEATURE:
              (A) NAME/KEY: Modified-site
              (B) LOCATION: 1
              (D) OTHER INFORMATION: /label= MODIFIED-SITE
                  /note= N-(aminoethyl)-N-(thymin-1-ylacetyl)-
                  glycine (ix) FEATURE:
              (A) NAME/KEY: Modified-site
              (B) LOCATION: 2
              (D) OTHER INFORMATION: /label= MODIFIED-SITE
                  /note= N-(aminoethyl)-N-(guanin-1-ylacetyl)-
                  glycine (ix) FEATURE:
              (A) NAME/KEY: Modified-site
              (B) LOCATION: 3
              (D) OTHER INFORMATION: /label= MODIFIED-SITE
                  /note= N-(aminoethyl)-N-(guanin-1-ylacetyl)-
                  glycine (ix) FEATURE:
              (A) NAME/KEY: Modified-site
              (B) LOCATION: 4
              (D) OTHER INFORMATION: /label= MODIFIED-SITE
                  /note= N-(aminoethyl)-N-(guanin-1-ylacetyl)-
                  glycine (ix) FEATURE:
              (A) NAME/KEY: Modified-site
              (B) LOCATION: 5
              (D) OTHER INFORMATION: /label= MODIFIED-SITE
                  /note= N-(2R-aminocyclohex-1R-yl)-N-(adenin-
                  1-ylacetyl)-glycine (ix) FEATURE:
              (A) NAME/KEY: Modified-site
              (B) LOCATION: 6
              (D) OTHER INFORMATION: /label= MODIFIED-SITE
```

-continued

```
            /note= N-(aminoethyl)-N-(guanin-1-ylacetyl)-
            glycine (ix) FEATURE:
     (A) NAME/KEY: Modified-site
     (B) LOCATION: 7
     (D) OTHER INFORMATION: /label= MODIFIED-SITE
            /note= N-(aminoethyl)-N-(cytosin-1-ylacetyl)-
            glycine (ix) FEATURE:
     (A) NAME/KEY: Modified-site
     (B) LOCATION: 8
     (D) OTHER INFORMATION: /label= MODIFIED-SITE
            /note= N-(2R-aminocyclohex-1R-yl)-N-(cytosin-
            1-ylacetyl)-glycine (ix) FEATURE:
     (A) NAME/KEY: Modified-site
     (B) LOCATION: 9
     (D) OTHER INFORMATION: /label= MODIFIED-SITE
            /note= N-(aminoethyl)-N-(adenin-1-ylacetyl)-
            glycine (ix) FEATURE:
     (A) NAME/KEY: Modified-site
     (B) LOCATION: 10
     (D) OTHER INFORMATION: /label= MODIFIED-SITE
            /note= N-(aminoethyl)-N-(thymin-1-ylacetyl)-
            glycine (ix) FEATURE:
     (A) NAME/KEY: Modified-site
     (B) LOCATION: 11
     (D) OTHER INFORMATION: /label= MODIFIED-SITE
            /note= N-(aminoethyl)-N-(adenin-1-ylacetyl)-
            glycine (ix) FEATURE:
     (A) NAME/KEY: Modified-site
     (B) LOCATION: 12
     (D) OTHER INFORMATION: /label= MODIFIED-SITE
            /note= N-(aminoethyl)-N-(guanin-1-ylacetyl)-
            glycine (ix) FEATURE:
     (A) NAME/KEY: Modified-site
     (B) LOCATION: 13
     (D) OTHER INFORMATION: /label= MODIFIED-SITE
            /note= N-(aminoethyl)-N-(cytosin-1-ylacetyl)-
            glycine (ix) FEATURE:
     (A) NAME/KEY: Modified-site
     (B) LOCATION: 14
     (D) OTHER INFORMATION: /label= MODIFIED-SITE
            /note= N-(aminoethyl)-N-(guanin-1-ylacetyl)-
            glycine (ix) FEATURE:
     (A) NAME/KEY: Modified-site
     (B) LOCATION: 15
     (D) OTHER INFORMATION: /label= MODIFIED-SITE
            /note= N-(aminoethyl)-N-(adenin-1-ylacetyl)-
            glycine (ix) FEATURE:
     (A) NAME/KEY: Modified-site
     (B) LOCATION: 16
     (D) OTHER INFORMATION: /label= MODIFIED-SITE
            /note= N-(aminoethyl)-N-(guanin-1-ylacetyl)-
            glycine (ix) FEATURE:
     (A) NAME/KEY: Modified-site
     (B) LOCATION: 17
     (D) OTHER INFORMATION: /label= MODIFIED-SITE
            /note= N-(aminoethyl)-N-(cytosin-1-ylacetyl)-
            glycine
```

-continued (ix) FEATURE:
           (A) NAME/KEY: Modified-site
           (B) LOCATION: 18
           (D) OTHER INFORMATION: /label= MODIFIED-SITE
               /note= N-(aminoethyl)-N-(cytosin-1-ylacetyl)-
               glycine (xi) SEQUENCE DESCRIPTION: SEQ ID NO:8:

Xaa Xaa Xaa Xaa Xaa Xaa Xaa Xaa Xaa Xaa Xaa Xaa Xaa Xaa
1               5                   10

Xaa Xaa Xaa Xaa
15

(2) INFORMATION FOR SEQ ID NO:9:

(i) SEQUENCE CHARACTERISTICS:
          (A) LENGTH: 22
          (B) TYPE: amino acid
          (C) STRANDEDNESS: single
          (D) TOPOLOGY: unknown (ii) MOLECULE TYPE: peptide (ix) FEATURE:
           (A) NAME/KEY: Modified-site
           (B) LOCATION: 1
           (D) OTHER INFORMATION: /label= MODIFIED-SITE
               /note= N-(aminoethyl)-N-(thymin-1-ylacetyl)-
               glycine (ix) FEATURE:
           (A) NAME/KEY: Modified-site
           (B) LOCATION: 2
           (D) OTHER INFORMATION: /label= MODIFIED-SITE
               /note= N-(aminoethyl)-N-(cytosin-1-ylacetyl)-
               glycine (ix) FEATURE:
           (A) NAME/KEY: Modified-site
           (B) LOCATION: 3
           (D) OTHER INFORMATION: /label= MODIFIED-SITE
               /note= N-(aminoethyl)-N-(thymin-1-ylacetyl)-
               glycine (ix) FEATURE:
           (A) NAME/KEY: Modified-site
           (B) LOCATION: 4
           (D) OTHER INFORMATION: /label= MODIFIED-SITE
               /note= N-(aminoethyl)-N-(guanin-1-ylacetyl)-
               glycine (ix) FEATURE:
           (A) NAME/KEY: Modified-site
           (B) LOCATION: 5
           (D) OTHER INFORMATION: /label= MODIFIED-SITE
               /note= N-(2S-aminocyclohex-1S-yl)-N-(adenin-
               1-ylacetyl)-glycine (ix) FEATURE:
           (A) NAME/KEY: Modified-site
           (B) LOCATION: 6
           (D) OTHER INFORMATION: /label= MODIFIED-SITE
               /note= N-(aminoethyl)-N-(guanin-1-ylacetyl)-
               glycine (ix) FEATURE:
           (A) NAME/KEY: Modified-site
           (B) LOCATION: 7
           (D) OTHER INFORMATION: /label= MODIFIED-SITE
               /note= N-(aminoethyl)-N-(thymin-1-ylacetyl)-
               glycine (ix) FEATURE:
           (A) NAME/KEY: Modified-site
           (B) LOCATION: 8
           (D) OTHER INFORMATION: /label= MODIFIED-SITE
               /note= N-(aminoethyl)-N-(adenin-1-ylacetyl)-

-continued

```
          glycine (ix) FEATURE:
     (A) NAME/KEY: Modified-site
     (B) LOCATION: 9
     (D) OTHER INFORMATION: /label= MODIFIED-SITE
         /note= N-(aminoethyl)-N-(guanin-1-ylacetyl)-
         glycine (ix) FEATURE:
     (A) NAME/KEY: Modified-site
     (B) LOCATION: 10
     (D) OTHER INFORMATION: /label= MODIFIED-SITE
         /note= N-(aminoethyl)-N-(cytosin-1-ylacetyl)-
         glycine (ix) FEATURE:
     (A) NAME/KEY: Modified-site
     (B) LOCATION: 11
     (D) OTHER INFORMATION: /label= MODIFIED-SITE
         /note= N-(aminoethyl)-N-(adenin-1-ylacetyl)-
         glycine (ix) FEATURE:
     (A) NAME/KEY: Modified-site
     (B) LOCATION: 12
     (D) OTHER INFORMATION: /label= MODIFIED-SITE
         /note= N-(aminoethyl)-N-(guanin-1-ylacetyl)-
         glycine (ix) FEATURE:
     (A) NAME/KEY: Modified-site
     (B) LOCATION: 13
     (D) OTHER INFORMATION: /label= MODIFIED-SITE
         /note= N-(aminoethyl)-N-(adenin-1-ylacetyl)-
         glycine (ix) FEATURE:
     (A) NAME/KEY: Modified-site
     (B) LOCATION: 14
     (D) OTHER INFORMATION: /label= MODIFIED-SITE
         /note= N-(aminoethyl)-N-(guanin-1-ylacetyl)-
         glycine (ix) FEATURE:
     (A) NAME/KEY: Modified-site
     (B) LOCATION: 15
     (D) OTHER INFORMATION: /label= MODIFIED-SITE
         /note= N-(aminoethyl)-N-(guanin-1-ylacetyl)-
         glycine (ix) FEATURE:
     (A) NAME/KEY: Modified-site
     (B) LOCATION: 16
     (D) OTHER INFORMATION: /label= MODIFIED-SITE
         /note= N-(aminoethyl)-N-(adenin-1-ylacetyl)-
         glycine (ix) FEATURE:
     (A) NAME/KEY: Modified-site
     (B) LOCATION: 17
     (D) OTHER INFORMATION: /label= MODIFIED-SITE
         /note= N-(2S-aminocyclohex-1S-yl)-N-(guanin-
         1-ylacetyl)-glycine (ix) FEATURE:
     (A) NAME/KEY: Modified-site
     (B) LOCATION: 18
     (D) OTHER INFORMATION: /label= MODIFIED-SITE
         /note= N-(aminoethyl)-N-(cytosin-1-ylacetyl)-
         glycine (ix) FEATURE:
     (A) NAME/KEY: Modified-site
     (B) LOCATION: 19
     (D) OTHER INFORMATION: /label= MODIFIED-SITE
         /note= N-(aminoethyl)-N-(thymin-1-ylacetyl)-
         glycine (ix) FEATURE:
```

```
          (A) NAME/KEY: Modified-site
          (B) LOCATION: 20
          (D) OTHER INFORMATION: /label= MODIFIED-SITE
              /note= N-(aminoethyl)-N-(adenin-1-ylacetyl)-
              glycine (ix) FEATURE:
          (A) NAME/KEY: Modified-site
          (B) LOCATION: 21
          (D) OTHER INFORMATION: /label= MODIFIED-SITE
              /note= N-(aminoethyl)-N-(adenin-1-ylacetyl)-
              glycine (ix) FEATURE:
          (A) NAME/KEY: Modified-site
          (B) LOCATION: 22
          (D) OTHER INFORMATION: /label= MODIFIED-SITE
              /note= N-(aminoethyl)-N-(guanin-1-ylacetyl)-
              glycine (xi) SEQUENCE DESCRIPTION: SEQ ID NO:9:

Xaa Xaa Xaa Xaa Xaa Xaa Xaa Xaa Xaa Xaa Xaa Xaa Xaa Xaa
 1               5                  10

Xaa Xaa Xaa Xaa Xaa Xaa Xaa Xaa
15                  20

(2) INFORMATION FOR SEQ ID NO:10:

(i) SEQUENCE CHARACTERISTICS:
          (A) LENGTH: 11
          (B) TYPE: amino acid
          (C) STRANDEDNESS: single
          (D) TOPOLOGY: unknown (ii) MOLECULE TYPE: peptide (ix) FEATURE:
          (A) NAME/KEY: Modified-site
          (B) LOCATION: 1
          (D) OTHER INFORMATION: /label= MODIFIED-SITE
              /note= N-(aminoethyl)-N-(thymin-1-ylacetyl)-
              glycine (ix) FEATURE:
          (A) NAME/KEY: Modified-site
          (B) LOCATION: 2
          (D) OTHER INFORMATION: /label= MODIFIED-SITE
              /note= N-(aminoethyl)-N-(thymin-1-ylacetyl)-
              glycine (ix) FEATURE:
          (A) NAME/KEY: Modified-site
          (B) LOCATION: 3
          (D) OTHER INFORMATION: /label= MODIFIED-SITE
              /note= N-(aminoethyl)-N-(thymin-1-ylacetyl)-
              glycine (ix) FEATURE:
          (A) NAME/KEY: Modified-site
          (B) LOCATION: 4
          (D) OTHER INFORMATION: /label= MODIFIED-SITE
              /note= N-(aminoethyl)-N-(thymin-1-ylacetyl)-
              glycine (ix) FEATURE:
          (A) NAME/KEY: Modified-site
          (B) LOCATION: 5
          (D) OTHER INFORMATION: /label= MODIFIED-SITE
              /note= N-(aminoethyl)-N-(thymin-1-ylacetyl)-
              glycine (ix) FEATURE:
          (A) NAME/KEY: Modified-site
          (B) LOCATION: 6
          (D) OTHER INFORMATION: /label= MODIFIED-SITE
              /note= N-(aminoethyl)-N-(thymin-1-ylacetyl)-
              glycine
```

```
    (ix) FEATURE:
         (A) NAME/KEY: Modified-site
         (B) LOCATION: 7
         (D) OTHER INFORMATION: /label= MODIFIED-SITE
             /note= N-(aminoethyl)-N-(thymin-1-ylacetyl)-
             glycine (ix) FEATURE:
         (A) NAME/KEY: Modified-site
         (B) LOCATION: 8
         (D) OTHER INFORMATION: /label= MODIFIED-SITE
             /note= N-(aminoethyl)-N-(thymin-1-ylacetyl)-
             glycine (ix) FEATURE:
         (A) NAME/KEY: Modified-site
         (B) LOCATION: 9
         (D) OTHER INFORMATION: /label= MODIFIED-SITE
             /note= N-(aminoethyl)-N-(thymin-1-ylacetyl)-
             glycine (ix) FEATURE:
         (A) NAME/KEY: Modified-site
         (B) LOCATION: 10
         (D) OTHER INFORMATION: /label= MODIFIED-SITE
             /note= N-(aminoethyl)-N-(thymin-1-ylacetyl)-
             glycine (xi) SEQUENCE DESCRIPTION: SEQ ID NO:10:

Xaa Xaa Xaa Xaa Xaa Xaa Xaa Xaa Xaa Xaa Lys
1               5                   10

(2) INFORMATION FOR SEQ ID NO: 11:

(i) SEQUENCE CHARACTERISTICS:
         (A) LENGTH: 10
         (B) TYPE: nucleic acid
         (C) STRANDEDNESS: single
         (D) TOPOLOGY: linear (xi) SEQUENCE DESCRIPTION:  SEQ ID NO: 11:

AAAAAAAAAA                                                                10

(2) INFORMATION FOR SEQ ID NO: 12:

(i) SEQUENCE CHARACTERISTICS:
         (A) LENGTH: 10
         (B) TYPE: nucleic acid
         (C) STRANDEDNESS: single
         (D) TOPOLOGY: linear (xi) SEQUENCE DESCRIPTION:  SEQ ID NO: 12:

AAAACAAAAA                                                                10

(2) INFORMATION FOR SEQ ID NO:13:

(i) SEQUENCE CHARACTERISTICS:
         (A) LENGTH: 11
         (B) TYPE: amino acid
         (C) STRANDEDNESS: single
         (D) TOPOLOGY: unknown (ii) MOLECULE TYPE: peptide (ix) FEATURE:
         (A) NAME/KEY: Modified-site
         (B) LOCATION: 1
         (D) OTHER INFORMATION: /label= MODIFIED-SITE
             /note N-(aminoethyl)-N-(guanin-1-ylacetyl)-
             glycine (ix) FEATURE:
         (A) NAME/KEY: Modified-site
```

```
            (B) LOCATION: 2
            (D) OTHER INFORMATION: /label= MODIFIED-SITE
                /note N-(2R-aminocyclohex-1R-yl)-N-(thymin-1-
                ylacetyl)-glycine (ix) FEATURE:
            (A) NAME/KEY: Modified-site
            (B) LOCATION: 3
            (D) OTHER INFORMATION: /label= MODIFIED-SITE
                /note N-(aminoethyl)-N-(adenin-1-ylacetyl)-
                glycine (ix) FEATURE:
            (A) NAME/KEY: Modified-site
            (B) LOCATION: 4
            (D) OTHER INFORMATION: /label= MODIFIED-SITE
                /note N-(aminoethyl)-N-(guanin-1-ylacetyl)-
                glycine (ix) FEATURE:
            (A) NAME/KEY: Modified-site
            (B) LOCATION: 5
            (D) OTHER INFORMATION: /label= MODIFIED-SITE
                /note N-(aminoethyl)-N-(adenin-1-ylacetyl)-
                glycine (ix) FEATURE:
            (A) NAME/KEY: Modified-site
            (B) LOCATION: 6
            (D) OTHER INFORMATION: /label= MODIFIED-SITE
                /note N-(2R-aminocyclohex-1R-yl)-N-(thymin-1-
                ylacetyl)-glycine (ix) FEATURE:
            (A) NAME/KEY: Modified-site
            (B) LOCATION: 7
            (D) OTHER INFORMATION: /label= MODIFIED-SITE
                /note N-(aminoethyl)-N-(cytosin-1-ylacetyl)-
                glycine (ix) FEATURE:
            (A) NAME/KEY: Modified-site
            (B) LOCATION: 8
            (D) OTHER INFORMATION: /label= MODIFIED-SITE
                /note N-(aminoethyl)-N-(adenin-1-ylacetyl)-
                glycine (ix) FEATURE:
            (A) NAME/KEY: Modified-site
            (B) LOCATION: 9
            (D) OTHER INFORMATION: /label= MODIFIED-SITE
                /note N-(aminoethyl)-N-(cytosin-1-ylacetyl)-
                glycine (ix) FEATURE:
            (A) NAME/KEY: Modified-site
            (B) LOCATION: 10
            (D) OTHER INFORMATION: /label= MODIFIED-SITE
                /note N-(2R-aminocyclohex-1R-yl)-N-(thymin-1-
                ylacetyl)-glycine (xi) SEQUENCE DESCRIPTION: SEQ ID NO:13:

Xaa Xaa Xaa Xaa Xaa Xaa Xaa Xaa Xaa Xaa Lys
1               5                   10

(2) INFORMATION FOR SEQ ID NO:14:

(i) SEQUENCE CHARACTERISTICS:
            (A) LENGTH: 11
            (B) TYPE: amino acid
            (C) STRANDEDNESS: single
            (D) TOPOLOGY: unknown (ii) MOLECULE TYPE: peptide (ix) FEATURE:
            (A) NAME/KEY: Modified-site
            (B) LOCATION: 1
```

(D) OTHER INFORMATION: /label= MODIFIED-SITE
                    /note N-(aminoethyl)-N-(guanin-1-ylacetyl)-
                    glycine (ix) FEATURE:
                (A) NAME/KEY: Modified-site
                (B) LOCATION: 2
                (D) OTHER INFORMATION: /label= MODIFIED-SITE
                    /note N-(2S-aminocyclohex-1S-yl)-N-(thymin-1-
                    ylacetyl)-glycine (ix) FEATURE:
                (A) NAME/KEY: Modified-site
                (B) LOCATION: 3
                (D) OTHER INFORMATION: /label= MODIFIED-SITE
                    /note N-(aminoethyl)-N-(adenin-1-ylacetyl)-
                    glycine (ix) FEATURE:
                (A) NAME/KEY: Modified-site
                (B) LOCATION: 4
                (D) OTHER INFORMATION: /label= MODIFIED-SITE
                    /note N-(aminoethyl)-N-(guanin-1-ylacetyl)-
                    glycine (ix) FEATURE:
                (A) NAME/KEY: Modified-site
                (B) LOCATION: 5
                (D) OTHER INFORMATION: /label= MODIFIED-SITE
                    /note N-(aminoethyl)-N-(adenin-1-ylacetyl)-
                    glycine (ix) FEATURE:
                (A) NAME/KEY: Modified-site
                (B) LOCATION: 6
                (D) OTHER INFORMATION: /label= MODIFIED-SITE
                    /note N-(2S-aminocyclohex-1S-yl)-N-(thymin-1-
                    ylacetyl)-glycine (ix) FEATURE:
                (A) NAME/KEY: Modified-site
                (B) LOCATION: 7
                (D) OTHER INFORMATION: /label= MODIFIED-SITE
                    /note N-(aminoethyl)-N-(cytosin-1-ylacetyl)-
                    glycine (ix) FEATURE:
                (A) NAME/KEY: Modified-site
                (B) LOCATION: 8
                (D) OTHER INFORMATION: /label= MODIFIED-SITE
                    /note N-(aminoethyl)-N-(adenin-1-ylacetyl)-
                    glycine (ix) FEATURE:
                (A) NAME/KEY: Modified-site
                (B) LOCATION: 9
                (D) OTHER INFORMATION: /label= MODIFIED-SITE
                    /note N-(aminoethyl)-N-(cytosin-1-ylacetyl)-
                    glycine (ix) FEATURE:
                (A) NAME/KEY: Modified-site
                (B) LOCATION: 10
                (D) OTHER INFORMATION: /label= MODIFIED-SITE
                    /note N-(2S-aminocyclohex-1S-yl)-N-(thymin-1-
                    ylacetyl)-glycine (xi) SEQUENCE DESCRIPTION: SEQ ID NO:14:

Xaa Xaa Xaa Xaa Xaa Xaa Xaa Xaa Xaa Xaa Lys
1               5                   10

(2) INFORMATION FOR SEQ ID NO:15:

(i) SEQUENCE CHARACTERISTICS:
                (A) LENGTH: 11
                (B) TYPE: amino acid
                (C) STRANDEDNESS: single
                (D) TOPOLOGY: unknown (ii) MOLECULE TYPE: peptide (ix) FEATURE:
             (A) NAME/KEY: Modified-site
             (B) LOCATION: 1
             (D) OTHER INFORMATION: /label= MODIFIED-SITE
                 /note N-(aminoethyl)-N-(guanin-1-ylacetyl)-
                 glycine (ix) FEATURE:
             (A) NAME/KEY: Modified-site
             (B) LOCATION: 2
             (D) OTHER INFORMATION: /label= MODIFIED-SITE
                 /note N-(aminoethyl)-N-(thymin-1- ylacetyl)-
                 glycine (ix) FEATURE:
             (A) NAME/KEY: Modified-site
             (B) LOCATION: 3
             (D) OTHER INFORMATION: /label= MODIFIED-SITE
                 /note N-(aminoethyl)-N-(adenin-1-ylacetyl)-
                 glycine (ix) FEATURE:
             (A) NAME/KEY: Modified-site
             (B) LOCATION: 4
             (D) OTHER INFORMATION: /label= MODIFIED-SITE
                 /note N-(aminoethyl)-N-(guanin-1-ylacetyl)-
                 glycine (ix) FEATURE:
             (A) NAME/KEY: Modified-site
             (B) LOCATION: 5
             (D) OTHER INFORMATION: /label= MODIFIED-SITE
                 /note N-(aminoethyl)-N-(adenin-1-ylacetyl)-
                 glycine (ix) FEATURE:
             (A) NAME/KEY: Modified-site
             (B) LOCATION: 6
             (D) OTHER INFORMATION: /label= MODIFIED-SITE
                 /note N-(aminoethyl)-N-(thymin-1-ylacetyl)-
                 glycine (ix) FEATURE:
             (A) NAME/KEY: Modified-site
             (B) LOCATION: 7
             (D) OTHER INFORMATION: /label= MODIFIED-SITE
                 /note N-(aminoethyl)-N-(cytosin-1-ylacetyl)-
                 glycine (ix) FEATURE:
             (A) NAME/KEY: Modified-site
             (B) LOCATION: 8
             (D) OTHER INFORMATION: /label= MODIFIED-SITE
                 /note N-(aminoethyl)-N-(adenin-1-ylacetyl)-
                 glycine (ix) FEATURE:
             (A) NAME/KEY: Modified-site
             (B) LOCATION: 9
             (D) OTHER INFORMATION: /label= MODIFIED-SITE
                 /note N-(aminoethyl)-N-(cytosin-1-ylacetyl)-
                 glycine (ix) FEATURE:
             (A) NAME/KEY: Modified-site
             (B) LOCATION: 10
             (D) OTHER INFORMATION: /label= MODIFIED-SITE
                 /note N-(aminoethyl)-N-(thymin-1- ylacetyl)-
                 glycine (xi) SEQUENCE DESCRIPTION: SEQ ID NO:15:

Xaa Xaa Xaa Xaa Xaa Xaa Xaa Xaa Xaa Xaa Lys
1               5                   10

(2) INFORMATION FOR SEQ ID NO: 16:

```
            (i) SEQUENCE CHARACTERISTICS:
                  (A) LENGTH: 9
                  (B) TYPE: nucleic acid
                  (C) STRANDEDNESS: single
                  (D) TOPOLOGY: linear (xi) SEQUENCE DESCRIPTION: SEQ ID NO: 16:

CATCTAGTG                                                                      9

(2) INFORMATION FOR SEQ ID NO: 17:

(i) SEQUENCE CHARACTERISTICS:
                  (A) LENGTH: 9
                  (B) TYPE: nucleic acid
                  (C) STRANDEDNESS: single
                  (D) TOPOLOGY: linear (xi) SEQUENCE DESCRIPTION: SEQ ID NO: 17:

CATCTGGTG                                                                      9
```